(12) United States Patent
Li et al.

(10) Patent No.: US 9,999,621 B2
(45) Date of Patent: Jun. 19, 2018

(54) MEDICAL USE OF ARTEMISININ COMPOUNDS AND GEPHYRIN AGONISTS

(71) Applicant: CeMM-Forschungszentrum für Molekulare Medizin GmbH, Vienna (AT)

(72) Inventors: Jin Li, Vienna (AT); Stefan Kubicek, Vienna (AT)

(73) Assignee: CeMM—Forschungszentrum für Molekulare Medizin GmbH, Vienna (AT)

( * ) Notice: Subject to any disclaimer, the term of this patent is extended or adjusted under 35 U.S.C. 154(b) by 0 days. days.

(21) Appl. No.: 15/303,170

(22) PCT Filed: Apr. 9, 2015

(86) PCT No.: PCT/EP2015/057755
§ 371 (c)(1),
(2) Date: Oct. 10, 2016

(87) PCT Pub. No.: WO2015/155303
PCT Pub. Date: Oct. 15, 2015

(65) Prior Publication Data
US 2017/0027929 A1 Feb. 2, 2017

(30) Foreign Application Priority Data

Apr. 11, 2014 (EP) .................................... 14164471

(51) Int. Cl.
| | |
|---|---|
| *A61K 31/4748* | (2006.01) |
| *A61K 31/155* | (2006.01) |
| *A61K 31/357* | (2006.01) |
| *A61K 31/366* | (2006.01) |
| *A61K 31/541* | (2006.01) |
| *A61K 38/28* | (2006.01) |
| *A61K 45/06* | (2006.01) |
| *G01N 33/50* | (2006.01) |
| *G01N 33/94* | (2006.01) |
| *G01N 1/30* | (2006.01) |

(52) U.S. Cl.
CPC ........ *A61K 31/4748* (2013.01); *A61K 31/155* (2013.01); *A61K 31/357* (2013.01); *A61K 31/366* (2013.01); *A61K 31/541* (2013.01); *A61K 38/28* (2013.01); *A61K 45/06* (2013.01); *G01N 33/502* (2013.01); *G01N 33/507* (2013.01); *G01N 33/9426* (2013.01); *G01N 1/30* (2013.01)

(58) Field of Classification Search
None
See application file for complete search history.

(56) References Cited

U.S. PATENT DOCUMENTS

2010/0151056 A1* 6/2010 Polansky .............. A23L 33/105
424/702

FOREIGN PATENT DOCUMENTS

| EP | 1978028 | 10/2008 |
|---|---|---|
| WO | WO 2012/033266 | 3/2012 |
| WO | WO 2014/007853 | 1/2014 |
| WO | WO 2014/048788 | 4/2014 |

OTHER PUBLICATIONS

Clark Jr., Charles M. Oral Therapy in Type 2 Diabetes: Pharmacological Properties and Clinical Use of Currently Available Agents. Diabetes Spectrum. 11(4), 1998, 211-221.*
Ahmad et al., "Evaluation of antidiabetic and antihyperlipidemic activity of *Artemisia indica linn* (aerial parts) in Streptozotocin induced diabetic rats," *Journal of Ethnopharmacology*, 151(1):618-623, 2014.
Davis, "Antimalarial drugs and glucose metabolism," *British Journal of Clinical Pharmacology*, 44(1):1-7, 1997.
Freeman et al., "Sleep fragmentation and motor restlessness in a *Drosophila* model of restless legs syndrome," *Current Biology*, 22(12):1142-1148, 2012.
Mannan et al., "Effects of vegetative and flowering stages on the biosynthesis of artemisinin in *Artemisia* species," *Archives of Pharmacal Research*, 34(10):1657-1661, 2011.
PCT International Search Report and Written Opinion issued in International Application No. PCT/EP2015/057755, dated Dec. 17, 2015.
Ribnicky et al., "Improved absorption and bioactivity of active compounds from an anti-diabetic extract of *Artemisia dracunculus* L.," *International Journal of Pharmaceutics*, 370(1-2):87-92, 2009.
Suckow et al., "Expression of neurexin, neuroligin, and their cytoplasmic binding partners in the pancreatic β-cells and the involvement of neuroligin in insulin secretion," *Endocrinology*, 149(12):6006-6017, 2008.
Suresh et al., "Phytochemical and pharmacological properties of *Artemisia pallens*," *International Journal of Pharmaceutical Sciences and Research*, 2(12):3081-3090, 2011.

* cited by examiner

*Primary Examiner* — Samantha L Shterengarts
(74) *Attorney, Agent, or Firm* — Parker Highlander PLLC

(57) ABSTRACT

The invention refers to BTBD9 binders and gephyrin binders for medical use and in particular an artemisinin compound of general formula I for use in the treatment of a diabetes patient, as well as a method of identifying suitable lead candidates.

21 Claims, 7 Drawing Sheets

Fig. 7. Primer sequences

Figure 1:
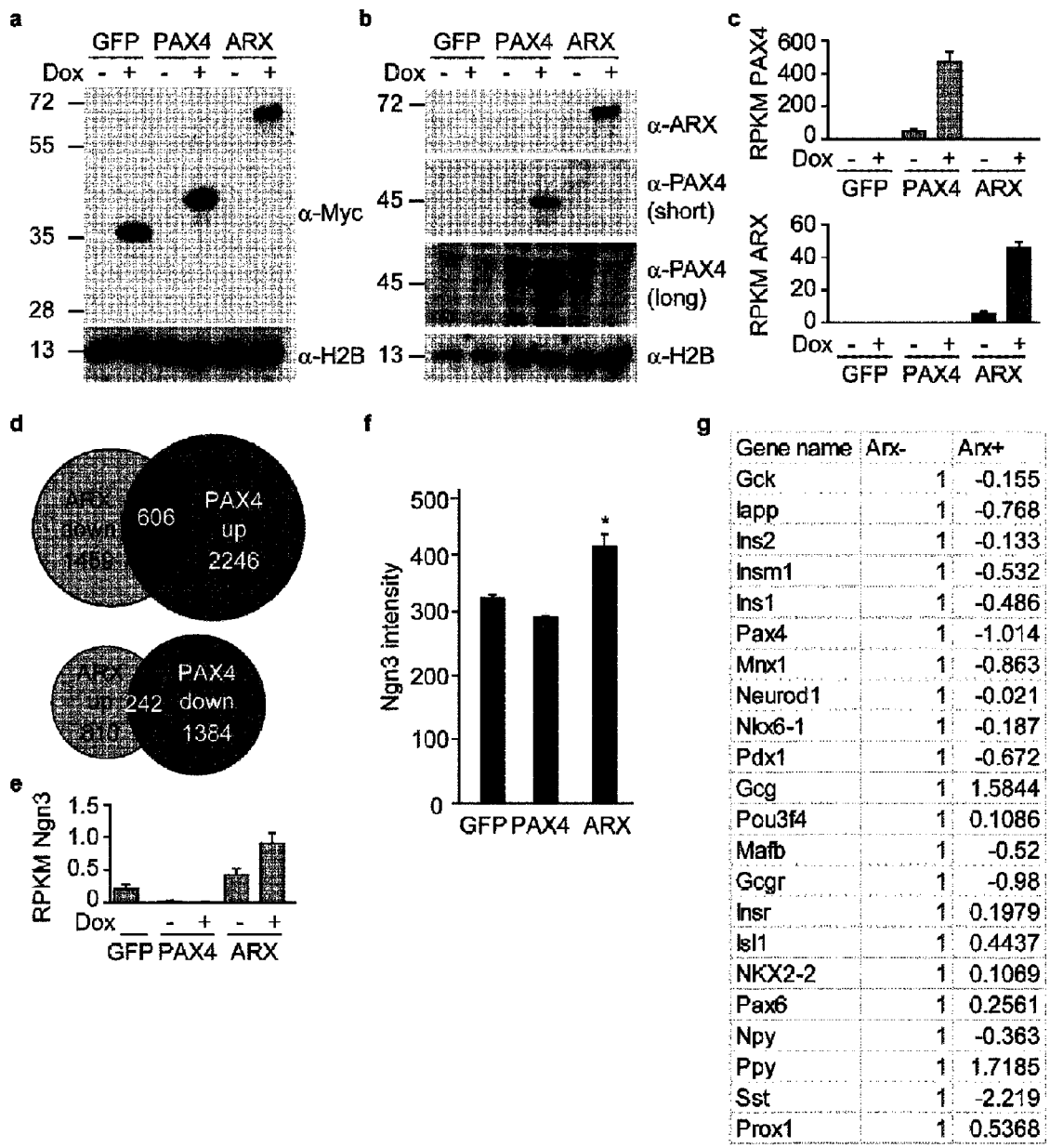

| Species | Gene | Orientation | Sequence | SEQ ID no |
|---|---|---|---|---|
| mm | Ins2 | fw | GTCAAGCAGCACCTTTGTGGTTCC | 1 |
| mm | Ins2 | re | ACAATGCCACGCTTCTGCTG | 2 |
| mm | Pdx1 | fw | TCCACCACCACCTTCCAGCTCA | 3 |
| mm | Pdx1 | re | AATTCCTTCTCCAGCTCCAG | 4 |
| mm | Rsk1 | fw | GCCGCTGGACCCGGAGAATG | 5 |
| mm | Rsk1 | re | GCCGGGTGACCTTGCGTACC | 6 |
| mm | Rsk2 | fw | TAACCGCAGAGGTCACACTCAG | 7 |
| mm | Rsk2 | re | CTCGAAACTGTGGCATCCCGA | 8 |
| mm | Rsk3 | fw | TGCTGGTGTTGATGGAGTGGAG | 9 |
| mm | Rsk3 | re | GGTCAAAGTGGAAGGTGTCCTC | 10 |
| mm | Actb | fw | GGTGGGAATGGGTCAGAAGGAC | 11 |
| mm | Actb | re | GGCCACACGCAGCTCATTGT | 12 |
| mm | Pax4 | fw | AGGTATCTAATGGCTGTGTGAGC | 13 |
| mm | Pax4 | re | GACACACTGGGAGCCTTGTC | 14 |
| mm | Npy | fw | TGGACTGACCCTCGCTCTAT | 15 |
| mm | Npy | re | TGTCTCAGGGCTGGATCTCT | 16 |
| mm | Iapp | fw | CTCTCTGTGGCACTGAACCA | 17 |
| mm | Iapp | re | GGACTGGACCAAGGTTGTTG | 18 |
| hs | GAPDH | fw | AGAAGGCTGGGGCTCATTTG | 19 |
| hs | GAPDH | re | AGGGGCCATCCACAGTCTTC | 20 |
| hs | TUBB3 | fw | CTCAGGGGCCTTTGGACATC | 21 |
| hs | TUBB3 | re | CAGGCAGTCGCAGTTTTCAC | 22 |
| hs | ACTB | fw | CTGTCTGGCGGCACCACCAT | 23 |
| hs | ACTB | re | GCAACTAAGTCATAGTCCGC | 24 |
| hs | HMBS | fw | GGCAATGCGGCTGCAA | 25 |
| hs | HMBS | re | GGGTACCCACGGGAATCAC | 26 |
| hs | SDHA | fw | TGGGAACAAGAGGGCATCTG | 27 |
| hs | SDHA | re | CCACCACTGCATCAAATTCATG | 28 |
| hs | AOF2 | fw | AATGCCAAAGCAGAGAAGGA | 29 |
| hs | AOF2 | re | CTGCAGTGTGCGGTTTCTAA | 30 |
| hs | INS | fw | CAGATCACTGTCCTTCTGCCATGG | 31 |
| hs | INS | re | GTTCCACAATGCCACGCTTC | 32 |
| hs | GCG | fw | TCCAGATCATTCTCAGCTTCCCAG | 33 |
| hs | GCG | re | CCTTCCTCGGCCTTTCACCA | 34 |
| hs | SST | fw | GCTGTCCTGCCGCCTCCAGT | 35 |
| hs | SST | re | CGTTCTCGGGGTGCCATAGC | 36 |
| hs | PPY | fw | TGTCCACCTGCGTGGCTCTGTT | 37 |
| hs | PPY | re | TATAAGTCCAGCGGGCTGAG | 38 |
| hs | PDX1 | fw | CCTTTCCCATGGATGAAGTC | 39 |
| hs | PDX1 | re | TTCAACATGACAGCCAGCTC | 40 |
| hs | MAFA | fw | AGTTGGCACTTCTCGCTCTC | 41 |
| hs | MAFA | re | TTCAGCAAGGAGGAGGTCAT | 42 |
| hs | ARX | fw | ATGAGGCTGGACTTGACCGAGG | 43 |
| hs | ARX | re | ACACTGCCGCTCCGAGGAAA | 44 |
| hs | PAX6 | fw | TCCATCAGACCCAGGGCAATC | 45 |
| hs | PAX6 | re | TAGGTTGCCCTGGCACCGAA | 46 |
| hs | AMY2A | fw | CTGGGTGGTGAGCCAATTAAAGC | 47 |
| hs | AMY2A | re | TGGTGGCCCAACCCAATCAT | 48 |
| hs | PAX4 | fw | GTGAGGGTCTGGTTTTCCAA | 49 |
| hs | PAX4 | re | AGGTGGGGTGTCACTCAGAC | 50 |

SEQUENCE LISTING

<160> NUMBER OF SEQ ID NOS: 50

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
gtcaagcagc acctttgtgg ttcc                                          24

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
acaatgccac gcttctgctg                                               20

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
tccaccacca ccttccagct ca                                            22

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
aattccttct ccagctccag                                               20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gccgctggac ccggagaatg                                               20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gccgggtgac cttgcgtacc                                               20

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
taaccgcaga ggtcacactc ag        22

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ctcgaaactg tggcatcccg a         21

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
tgctggtgtt gatggagtgg ag        22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
ggtcaaagtg gaaggtgtcc tc        22

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
ggtgggaatg ggtcagaagg ac        22

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ggccacacgc agctcattgt           20

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
aggtatctaa tggctgtgtg agc       23

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gacacactgg gagccttgtc                    20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tggactgacc ctcgctctat                    20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tgtctcaggg ctggatctct                    20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ctctctgtgg cactgaacca                    20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ggactggacc aaggttgttg                    20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
agaaggctgg ggctcatttg                    20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
aggggccatc cacagtcttc						20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ctcaggggcc tttggacatc						20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
caggcagtcg cagttttcac						20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ctgtctggcg gcaccaccat						20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gcaactaagt catagtccgc						20

<210> SEQ ID NO 25
<211> LENGTH: 16
<212> TYPE: DNA
<213> ORGANISM: Artificial Sequence
<220> FEATURE:
<223> OTHER INFORMATION: Primer

<400> SEQUENCE: 25
ggcaatgcgg ctgcaa						16

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
gggtacccac gggaatcac						19

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tgggaacaag agggcatctg                                          20

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
ccaccactgc atcaaattca tg                                       22

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
aatgccaaag cagagaagga                                          20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
ctgcagtgtg cggtttctaa                                          20

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
cagatcactg tccttctgcc atgg                                     24

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gttccacaat gccacgcttc                                          20

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
tccagatcat tctcagcttc ccag                                          24

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
ccttcctcgg cctttcacca                                               20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
gctgtcctgc cgcctccagt                                               20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
cgttctcggg gtgccatagc                                               20

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
tgtccacctg cgtggctctg tt                                            22

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tataagtcca gcgggctgag                                               20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
cctttcccat ggatgaagtc                                               20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
ttcaacatga cagccagctc                                               20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
agttggcact tctcgctctc                                               20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
ttcagcaagg aggaggtcat                                               20

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
atgaggctgg acttgaccga gg                                            22

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
acactgccgc tccgaggaaa                                               20

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
tccatcagac ccagggcaat c                                             21

<210> SEQ ID NO 46
<211> LENGTH: 20
<212> TYPE: DNA
<213> ORGANISM: Artificial Sequence
<220> FEATURE:
<223> OTHER INFORMATION: Primer

```
<400> SEQUENCE: 46
taggttgccc tggcaccgaa                                                20

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
ctgggtggtg agccaattaa aagc                                           24

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
tggtggccca acccaatcat                                                20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
gtgagggtct ggttttccaa                                                20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
aggtggggtg tcactcagac                                                20
```

MEDICAL USE OF ARTEMISININ COMPOUNDS AND GEPHYRIN AGONISTS

This application is a national phase application under 35 U.S.C. § 371 of International Application No. PCT/EP2015/057755, filed Apr. 9, 2015, which claims benefit of European Application No. 14164471.6, filed Apr. 11, 2014, the entire contents of each of which are hereby incorporated by reference.

The invention relates to an artemisinin compound for use in the treatment of a diabetes patient, and further the medical use of gephyrin agonistic agents.

BACKGROUND

Type 1 diabetes patients have often lost all functional beta cells, as indicated by the complete absence of insulin C-peptide from their serum. Pancreatic islet transplantation has been shown to be curative in essence, but is limited by the availability of donor islets, immunological complications and transplant survival. Therefore, attempts to regenerate patient-specific insulin-producing cells have been undertaken using different tissue sources, including embryonal stem cells (ES), induced pluripotent stem cells (iPS), hepatic, exocrine, and alpha cells (Al-Hasani et al., 2013; Collombat et al., 2009; Zhou et al., 2008). In most cases, the approaches to increase beta cell mass have relied on the overexpression of master regulatory transcription factors involved in normal pancreas development, and in only a few cases small molecules or biologicals have been used. Alpha cells are a particularly attractive starting point as they are developmentally closely related to beta cells. These cells have been shown to be able to replenish insulin-producing cell mass following extreme beta cell loss. In a genetic model, overexpression of the transcription factor Pax4 can convert mouse alpha cells to beta cells during development (Collombat et al., 2009) and when triggered in adulthood (Al-Hasani et al., 2013). Molecularly, the beta cell factor Pax4 acts by directly repressing the alpha cell master regulatory transcription factor Arx and loss of Arx alone is sufficient to convert alpha into beta cells (Courtney et al., 2013).

Some antidiabetic treatments employ plant extracts; more than 800 plants have been reported to have antihyperglycemic effects with less adverse effects and low toxicity as compared to synthetic compounds. For example, extraction of aerial parts of *Artemisia indica* is e.g. described by Ahmad et al. (2014). Major functions of such extracts are found to be based on protective effects of major tissues such as kidney, liver and pancreas.

Artemisinin is a sesquiterpene lactone endoperoxide extracted and isolated from the leaves of *Artemisia annua*, and well-known as an antimalarial medicine. Artemisinin and its derivatives are described in the WHO monograph on good agricultural and collection practices (GACP) for *Artemisia annua L.* (WHO monograph 2006).

In a completely different field, namely the field of GABA receptors (i.e. receptors of the gamma-aminobutyric acid, herein called GABAR) which is an ionotropic receptor and ligand-gated ion channel, and its endogenous ligand which is gamma-aminobutyric acid (GABA) the mechanisms of GABAergic synapse formation and plasticity and the role of GABA receptor in the regulation of adult neurogenesis was subject to investigations to understand CNS function (Tyagarajan et al., 2010). Gephyrin is considered a scaffolding molecule of inhibitory synapsis and contributing to GABAR clustering. BTB domain proteins are known to interact with Cullin family ubiquitin ligases and are responsible for targeting specific substrate proteins for ubiquitination and subsequent degradation. (Stogios et al. Genome biology 2005, Genau et al. Mol. Cell 2015). GABA receptors are known to be ubiquitinated (Arancibia-Cárcamo et al. PNAS 2009).

WO 2012/033266 A1 describes specific artemisinin derivatives which are specific glycolipid hybrid derivatives, their antiangiogenic activity and use in preventing and treating angiogenic disease, among them angiogenic disease associated with diabetes.

Davis et al. (Br. J. Clin. Pharmacol. 1997, 44(1):1-7) describe the potential effect of antimalarial drugs on plasma glucose and insulin concentration.

Suresh et al. (International Journal of Pharmaceutical Sciences and Research 2011, 3081) describe phytochemical and pharmacological properties of *Artemisia pallens*, Walls. Ex DC, commonly known as Davana, an aromatic herb found in India, that has been used for the treatment of diabetes mellitus.

Ahmad et al. (Journal of Ethnopharmacology 2014, 151 (1): 618-623) describe antidiabetic activity of *Artemisia indica* linn (aerial parts) in Streptozotin induced diabetic rats.

Ribnicky et al. (International Journal of Pharmaceutics 2009, 370(1-2):87-92) describe an anti-diabetic extract of *Artemisia dracunculus*.

Mannan et al. (Archives of Pharmaceutical Research 2011, 34(10):1657-1661) describe the biosynthesis of artemisinin in several *Artemisia* species.

WO2014/048788A1 describes the production of pancreatic beta-cells by inhibiting the expression or the activity of Arx in a population of pancreatic alpha-cells.

Suckow et al. (Endocrinology 2008, 149(12):6006-6017) describe the pancreatic beta-cells exocytic machinery and the developmental pathway of beta-cells.

WO2014/007853A1 describes dihydromyricitin for the treatment of diseases and disorders of the glutamatergic system.

SUMMARY OF THE INVENTION

It is the objective of the present invention to identify compounds which have a potential to induce or enhance insulin production in pancreatic cells, and which have the potential to be used as a medicament based on a novel mode of action.

The object is solved by the subject of the present invention.

According to the invention there is provided an artemisinin compound for use in the treatment of a diabetes patient, such as to increase the insulin level, in particular to increase the number of beta cells, the insulin expression or the glucose-dependent blood insulin level in the patient, which compound is of general formula I

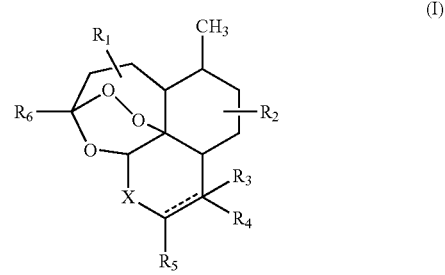

wherein

----- is a single or double bond;

$R_1$, $R_2$, $R_3$, $R_4$, and $R_6$ represent independently from one another H, halogen, —$CF_3$, =$CH_2$, —$OR^a$, —$NR^aR^b$, —$(CH_2)_nCOOR^a$, —$(CH_2)_nC(=O)R^a$, —$(CH_2)_nCONR^aR^a$, $C_{1-6}$alkyl, $C_{2-6}$alkenyl, $C_{2-6}$alkynyl, $C_{3-7}$cycloalkyl, $C_{3-7}$heterocycloalkyl, aryl and heteroaryl; and $R_5$ represents H, halogen, =O, —$OR^a$, —$NR^aR^b$, —$(CH_2)_nCF_3$, —$(CH_2)_nCHF_2$, —$(CH_2)_n$ C(=O)$R^a$, —O($CH_2)_nCOOR^a$, —OC(=O)($CH_2)_nCOOR^a$, —OC(=O)$R^a$, $C_{1-6}$alkyl, $C_{2-6}$alkenyl, $C_{2-6}$alkynyl, $C_{3-7}$cycloalkyl, $C_{3-7}$heterocycloalkyl, aryl and heteroaryl; and X represents O or —$NR^a$, $R^a$ represents H or optionally substituted $C_{1-6}$alkyl, $C_{2-6}$alkenyl, or $C_{2-6}$alkynyl; and $R^b$ represents H or an optionally substituted $C_{1-6}$alkyl, $C_{2-6}$alkenyl, $C_{2-6}$alkynyl, cycloalkyl, aryl, heteroaryl or aralkyl; or $R^a$ and $R^b$ together with the interjacent nitrogen atom represent a heterocyclic group, wherein the heterocyclic atom is N, O or S; and wherein the heterocyclic atom is optionally substituted (artemisone); and n is 0, 1, 2 or 3.

Specifically, the artemisinin compound is no artemsinin derivative which is a hybrid with a glycolipid component.

The artemisinin compound is specifically used in a method for treating a patient suffering from diabetes or a diabetes associated disorder, e.g. diabetes type I, diabetes type 2, a C-peptide negative or positive diabetes, or diabetes-associated disorders.

Specifically, the compound is administered to the patient in a therapeutically effective amount to increase the insuling expression or level, in particular to treat hypoinsulinemia, preferably by systemic or local administration.

According to a specific aspect, the compound is selected from the group consisting of artelinic acid, artemether, artemotil (arteether, β-arteether), artenimol (dihydroartemisinin, β-dihydroartemisinin), artemisone, and artesunate, or a pharmaceutically acceptable salt thereof.

Specifically, the compound is coupled to a ligand or carrier moiety.

Specific embodiments refer to the treatment wherein the compound is administered in a pharmaceutical preparation for oral, parenteral, systemic, mucosal, topic, rectal, sublingual, buccal or implant use which preparation comprises a pharmaceutically acceptable carrier, preferably wherein the pharmaceutical preparation is a tablet, dermal or transdermal formulation, ointment, gel, cream, lotion, patch, solution, injectable, ophtalmic solution, disperse system, emulsion, microencapsulated drug system, osmotic pump, subdermal implant, granule, microsphere, modified-release system, targeted release system, granules, or pill.

According to a specific aspect, the compound is administered at a dose at least once per day, preferably at a dose of 0.01-2000 mg/day, preferably 0.1-500 mg/day, in a single dose or multiple doses, or wherein the dose is provided in a slow-release formulation or device. Such doses are specifically indicated for oral administration.

According to a specific embodiment, the treatment is combined with another anti-diabetic therapy, preferably treatment with an antidiabetic agent, preferably any of insulin, sulfonylureas, incretins, other secretagogues, glitazones, metformin, GLP-1 agonists or DPP4 inhibitors, glucosidease inhibitors, amylin analogs, SGLT2 inhibitors, gastric bypass surgery or pancreatic island transplantation.

According to another specific embodiment, the treatment is combined with an immunomodulatory drug, including vaccine-based approaches using beta cell autoantigens, anti-CD3 antibodies, anti-CD20 antibodies, anti-CTLA4 antibodies, nicotinamide, rapamycin, cyclosporine A, azatiopirine, anti-thymocyte globulin (ATG), or prednisolone.

Specifically, the compound is administered in combination with another gephyrin agonist or an inhibitor of the human BTB (POZ) domain containing 9 (BTBD9, Gene ID 114781).

According to the invention, there is further provided a pharmaceutical combination preparation, in particular for treating a diabetes patient or any other medical use to increase the insulin level, comprising a) an artemisinin compound of general formula I; and
b) another BTBD9 inhibitor or gephyrin agonist which is an agent that i) inhibits the binding of BTBD9 to CUL3 (human cullin 3, Gene ID: 8452); and/or
ii) increases the level or clustering of gephyrin; and/or
iii) increases, enhances, stimulates, or promotes binding of gephyrin to the receptor of the gamma-aminobutyric acid (GABAR, multi-subunit complex made up of different combinations of subsets of the proteins encoded by Gene IDs: 2550, 2554, _2555, 2556, 2557, 2558, 2559, 2560, 2561, 2562, 2563, 2564 2565, 2566, 2567, 2568, 2569, 2570, 9568, 55879, 200959); and/or
iv) increases gephyrin-mediated signaling of the GABAR.

According to the invention, there is further provided a method for identifying a lead candidate agent that is effective in treating diabetes in a patient, the method comprising: screening one or more test agents in a cell-based assay, comprising the steps:

a) providing a pancreatic alpha-cell or a pancreatic beta-cell that overexpresses ARX;
b) contacting the cell with a test agent; and
c) detecting if the test agent
i) increases insulin expression by said cell; and/or
ii) represses ARX in said cell; and/or
iii) inhibits the interaction of BTBD9 with CUL3
iv) increases the level or clustering of gephyrin; and/or
v) increases gephyrin-mediated signaling of the GABAR;

thereby identifying a lead candidate agent for treating diabetes.

Specifically, the test agent is selected from the group consisting of small molecules, peptides, proteins, protein domains, such as antibodies or antibody fragments, aptamers, and nucleic acids, preferably a test agent obtained by screening a library of test agents.

According to the invention, there is further provided a method of identifying a lead candidate agent for medical use, the method comprising: screening one or more test agents in a cell-based assay, comprising the steps:

a) contacting a mammalian cell with a test agent under conditions allowing interaction of the test agent with BTBD9 or gephyrin produced by the cell; and
b) determining if the test agent
i) increases the thermal stability of BTBD9; and/or
ii) inhibits the binding of BTBD9 to CUL3; and/or
iii) increases the level or clustering of gephyrin; and/or
iv) increases, enhances, stimulates, or promotes binding of gephyrin to GABAR; and/or
v) increases gephyrin-mediated signaling of the GABAR, thereby identifying a lead candidate agent for medical use, in particular for the treatment of diabetes or anti-diabetic use.

According to the invention, there is further provided a BTBD9 binding or gephyrin binding active agent, for use in the treatment of a diabetes patient to increase the insulin level, preferably wherein the active agent is a small molecule. Exemplary BTBD9 binding or gephyrin binding small molecules are e.g. any of the artemisinin compounds of the invention. Alternative small molecules may be screened from appropriate sources, e.g. large libraries of small molecules employing binding assays and functional tests. Such active agents particularly would inhibit BTBD9 to indirectly agonise gephyrin by inhibiting its degradation functionally activating gephyrin, or directly bind and agonise gephyrin.

According to the invention, there is further provided a BTBD9 binding or gephyrin binding active agent for medical use, except an agent which is an artemisinin compound for anti-infectious or antimicrobial use. Optional further exceptions would be prior art artemisinin compounds for treatment of skin diseases, cancer, Trauma Haemorrhage and Associated Conditions, Myocardial Infarction and Coronary Heart Disease, Hemorrhoids, Alzheimer Disease, Crohn's Disease.

Specifically, the BTBD9 binding or gephyrin binding active agent is provided for use in the treatment of a disease other than infectious disease.

Specific exceptions would refer to an artemisinin compound for anti-infectious or antimicrobial use, or optionally for use in the treatment of one or more of the diseases selected from the group consisting of skin diseases, cancer, Trauma Haemorrhage and Associated Conditions, Myocardial Infarction and Coronary Heart Disease, Hemorrhoids, Alzheimer Disease, and Crohn's Disease, wherein the artemisinin compound is selected from the group consisting of artelinic acid, artemether, artemotil, artenimol, artemisone and artesunate, or a pharmaceutically acceptable salt thereof, or specifically wherein said artemisinin compound is any artemisinin compound of formula I. Specifically such gephyrin binding active agent is any other than an artemisinin compound for use in the treatment of malaria or an infectious disease.

According to one aspect, any such gephyrin binding active agent including artemisinin compounds and/or any other BTBD9 binding or gephyrin binding active agent may be used for treatment of a diabetic patient.

According to a further specific aspect, any such BTBD9 binding or gephyrin binding active agent including artemisinin compounds and/or any other gephyrin binding active agent may be used for treating a patient suffering from a medical disorder or disease other than diabetes, however, excluding anti-infectious or antimicrobial use, optionally further excluding treatment of skin diseases or cancer.

Exemplary medical use other than anti-diabetic use is for treatment of autoimmune disease, a neurological disorder including temporal lobe epilepsy, sleep disorders, panic attacks, seizures, muscle spasms, Moco deficiency or alcoholism.

According to a further specific aspect, any such BTBD9 binding or gephyrin binding active agent other than artemisinin compounds may be used for treatment of a diabetic patient or a patient suffering from any other medical disorder or disease. Exemplary medical use other than anti-diabetic use is anti-infectious or antimicrobial use, e.g. including treatment of an infectious disease, such as malaria, or for treatment of autoimmune disease, a neurological disorder including temporal lobe epilepsy, sleep disorders, panic attacks, seizures, muscle spasms, Moco deficiency or alcoholism.

Accordingly, there is provided a method of treating either a diabetes patient to increase the insulin level of said patient, or a patient suffering from a disease other than infectious disease, by administering an effective amount of a BTBD9 binding or gephyrin binding active agent, in particular a BTBD9 inhibitor or a gephyrin agonizing agent, preferably organic small molecules.

According to a specific aspect, there is further provided a pharmaceutical preparation comprising a BTBD9 binding or gephyrin binding agent as an active agent, and a pharmaceutically acceptable carrier, which agent is any other than an artemisinin compound, for example a small molecule capable of binding to BTBD9 or gephyrin, except an artemisinin compound which is selected from the group consisting of artelinic acid, artemether, artemotil, artenimol, artemisone and artesunate, or a pharmaceutically acceptable salt thereof, or specifically any other than an artemisinin compound which is any artemisinin compound of formula I.

According to a specific aspect, the invention further provides for a pharmaceutical combination product comprising a) a BTBD9 binding or gephyrin binding agent, such as preferably an artemisinin compound; and b) an antidiabetic agent, such as preferably any of insulin, sulfonylureas, incretins, other secretagogues, glitazones, metformin, GLP-1 agonists, DPP4 inhibitors, glucosidease inhibitors, amylin analogs, or SGLT2 inhibitors, and/or c) an immunomodulatory drug, including vaccine-based approaches using beta cell autoantigens, anti-CD3 antibodies, anti-CD20 antibodies, anti-CTLA4 antibodies, nicotinamide, rapamycin, cyclosporine A, azatiopirine, anti-thymocyte globulin (ATG), or prednisolone.

Such combination product may specifically be provided as a mixture, or as a kit of parts.

FIGURES

FIG. 1. A cellular model for pancreatic transdifferenation by PAX4 and ARX. a. Inducibility of GFP (control), PAX4 and ARX following 24 hours induction of the Myc-tagged overexpression constructs by 1 ug/ml doxycycline in conditional Min6-tet on cell lines. Histone H2B is used as a loading control. b. Western blots with antibodies detecting the overexpressed ARX and PAX4 proteins. ARX overexpression appears to reduce levels of endogenous PAX4 as detected after long exposure. c. Analysis of RNA-Sequencing data in these cell lines, indicating transcript abundance of PAX4 and ARX determined as reads per kilobase per million mapped reads (RPKM). d. Venn diagram representing genes significantly changed (p-value<0.05) between transcription factor induced and GFP induced cells at 24 hours. e. Ngn3 RNA levels are oppositelty regulated after 24 h ARX and PAX4 overexpression. f. Ngn3 protein detected by immunofluorescence is upregulated following ARX overexpression for 24 h. g. Log 2-fold expression change of pancreatic endocrine factors upon Arx overexpression for 144 hours, investigated by RNA-seq in three different single cell clones.

Figure 2:
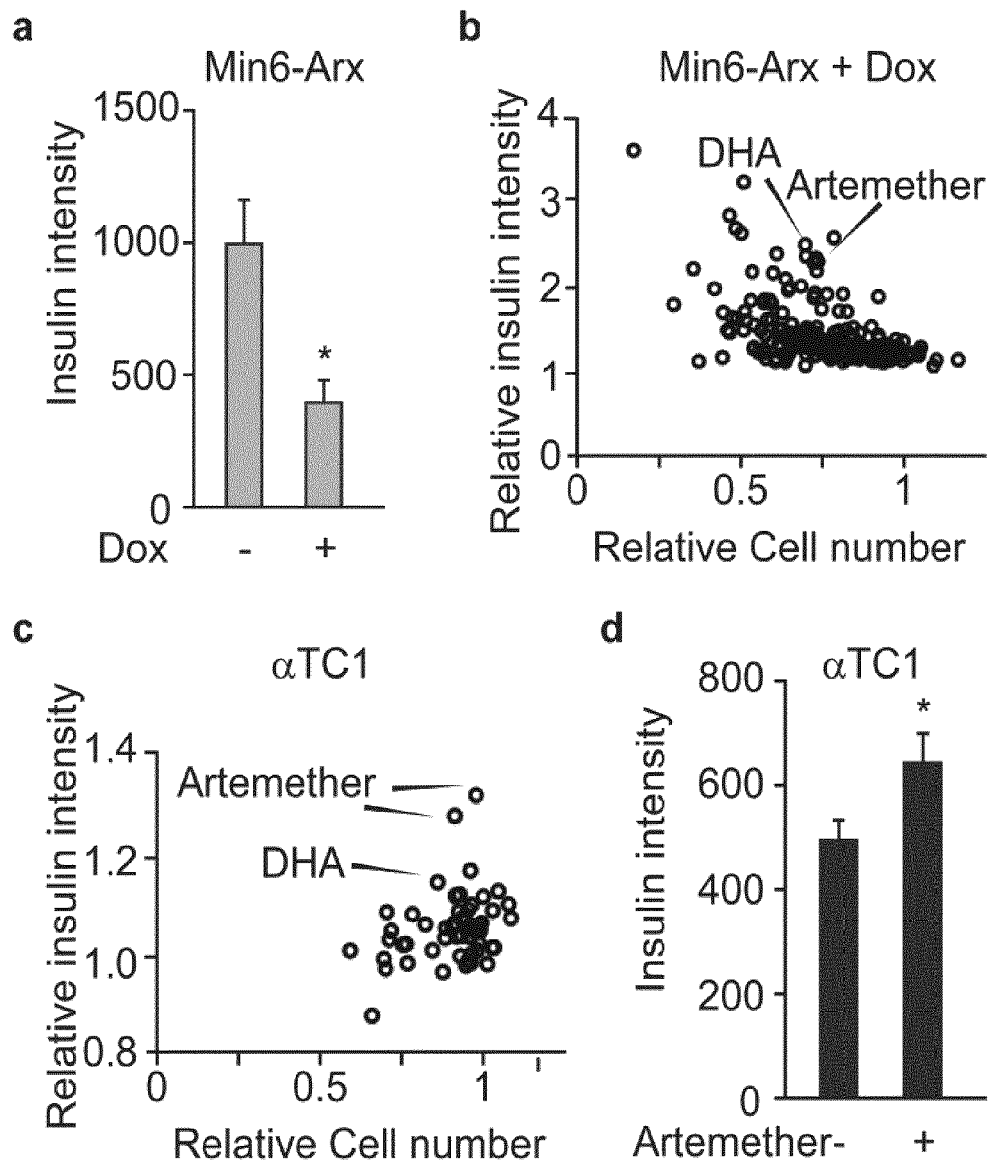

FIG. 2. A high throughput screen for functional repressors of ARX a. ARX overexpression for 3 days in Min6 cells lowers insulin protein levels as detected by immunofluorescence staining. *, p<0.01 compared to uninduced cells. b. Overview of screening data in Min6 cells induced to overexpress ARX. c. Validation of hits from the primary screen by immunofluorescence staining of alpha cell line aTC1 for insulin protein. d. Artemether treatment increases insulin protein levels in alphaTC1 cells, detected by immunofluorescence. *, p<0.01 compared to control.

Figure 3:
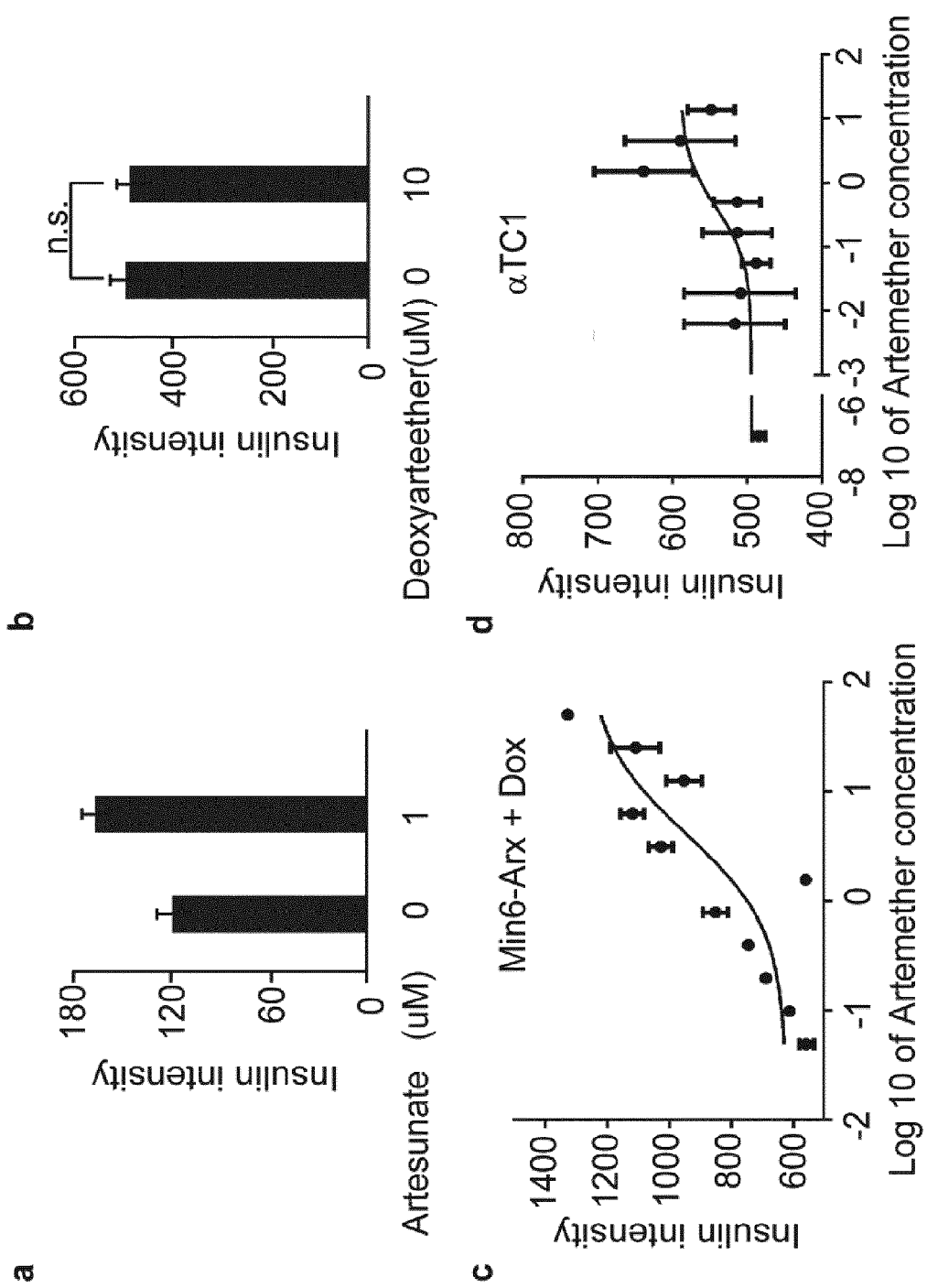

FIG. 3. Activity of artemisinins in alpha cells. a. Artesunate is also active in inducing insulin expression in alpha cell. b. Artemisin analog deoxyarteether lacking the endoperoxie moiety is inactive. c. Dose response of artemether in Min6 cells overexpressing ARX detected by immunofluorescence. d. Dose response of artemether in inducing insulin expression in alpha cell detected by immunofluorescence.

Figure 4:
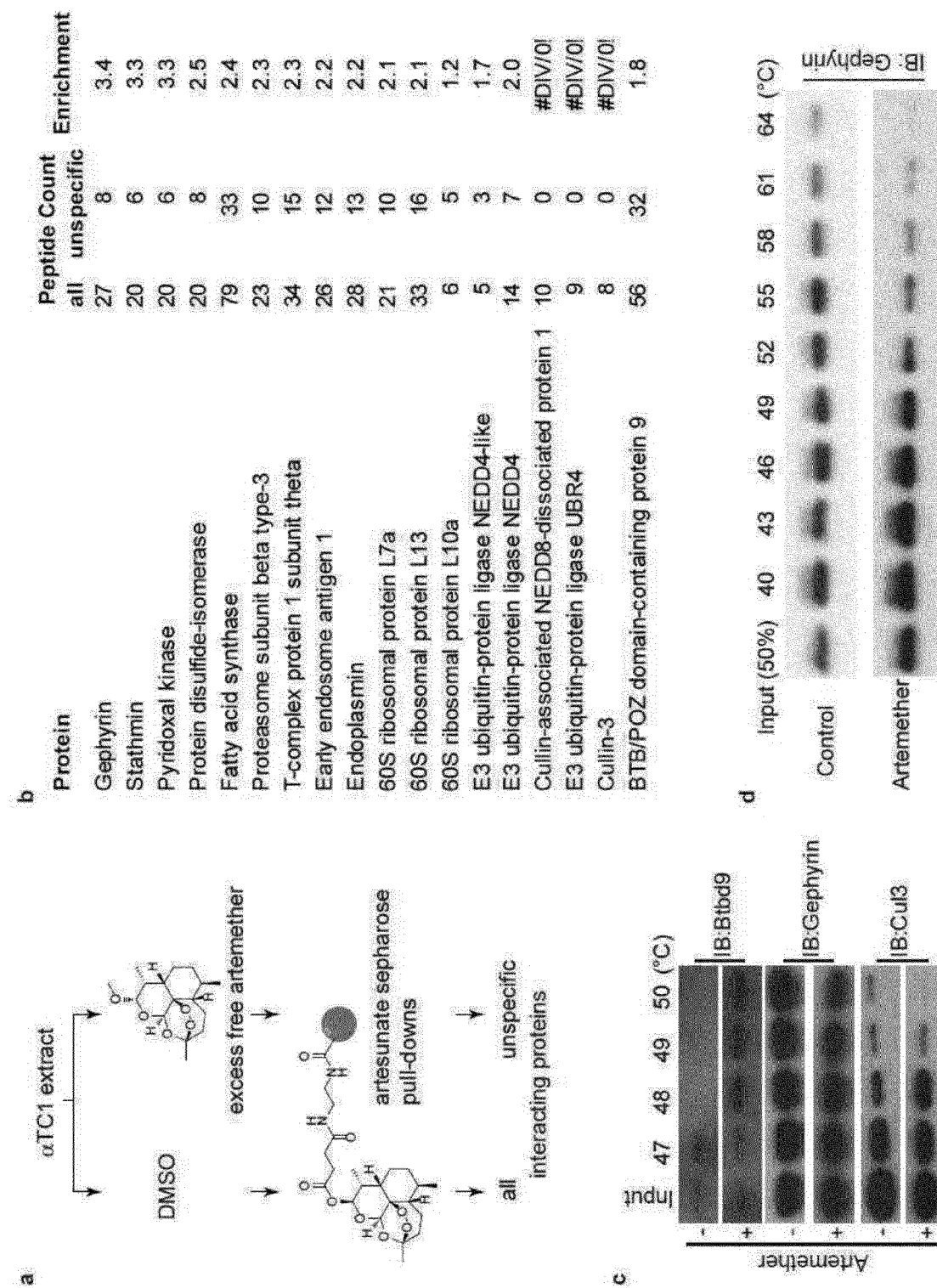

FIG. 4. Btbd9 and gephyrin are mammalian targets of artemisinins a. Outline of the chemical proteomics assay. b. List of proteins identified with significant enrichment over the competition experiment. c. Artemether results in changes in the thermal stability of Btbd9 and Cul3 in a cellular thermoshift assay. d. Artemether reduces the thermal stability of gephyrin in a cellular thermoshift assay.

Figure 5:
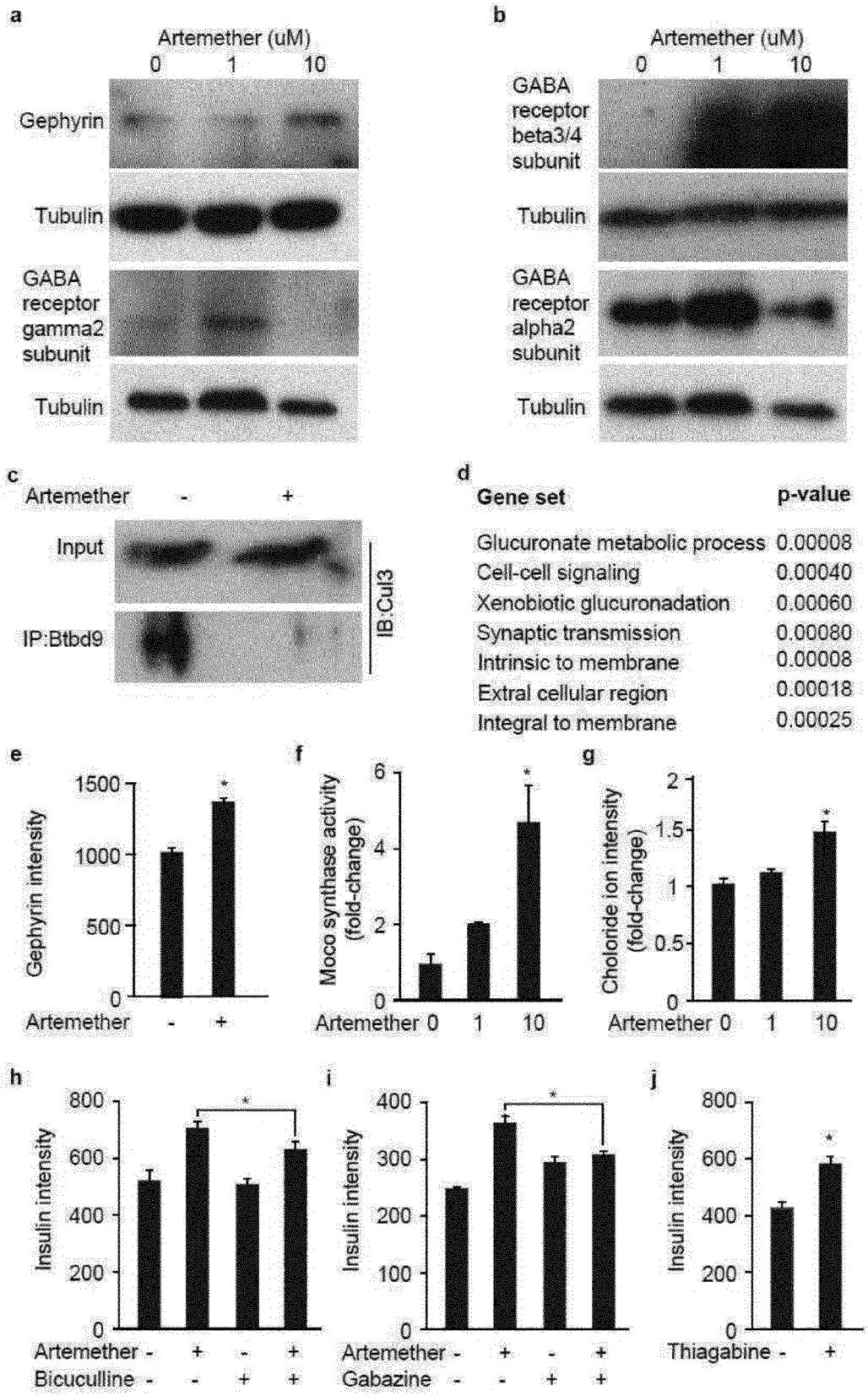

FIG. 5. Artemisinins inhibit the Btbd9-Cul3 interaction, stabilize gephyrin and activate GABA signaling. a. Western blots for gephyrin and GABA receptor subunits in aTC1 cells treated with artemether. b. Western blot for GABAR in aTC1 cells treated with artemether. c. Immunoprecipitation in aTC1 lysates identifies artemether to in inhibit the interaction between Btbd9 and Cul3. d. Gene set enrichment analysis of GO terms associated with genes up-regulated by Artemether treatment of aTC1 cells. e. Artemether increases gephyrin protein levels in alpha cells as detected by immunofluorescence. f. Artemether treatment increases Moco synthase activity of gephyrin. g. Artemether increases intracellular chloride concentration. h. GABAR antagonist Biculine inhibits the effects of Artemether on aTC1 cells, detected by immunofluorescence. *, $p<0.01$ compared to Artemether-only treated cells. i. GABAR antagonist Gabazine inhibits the effects of Artemether on aTC1 cells, detected by immunofluorescence. *, $p<0.01$ compared to Artemether-only treated cells. j. GABAR agonist Thiagabine increases insulin production in aTC1 cells, detected by immunofluorescence. *, $p<0.01$ compared to control.

Figure 6:
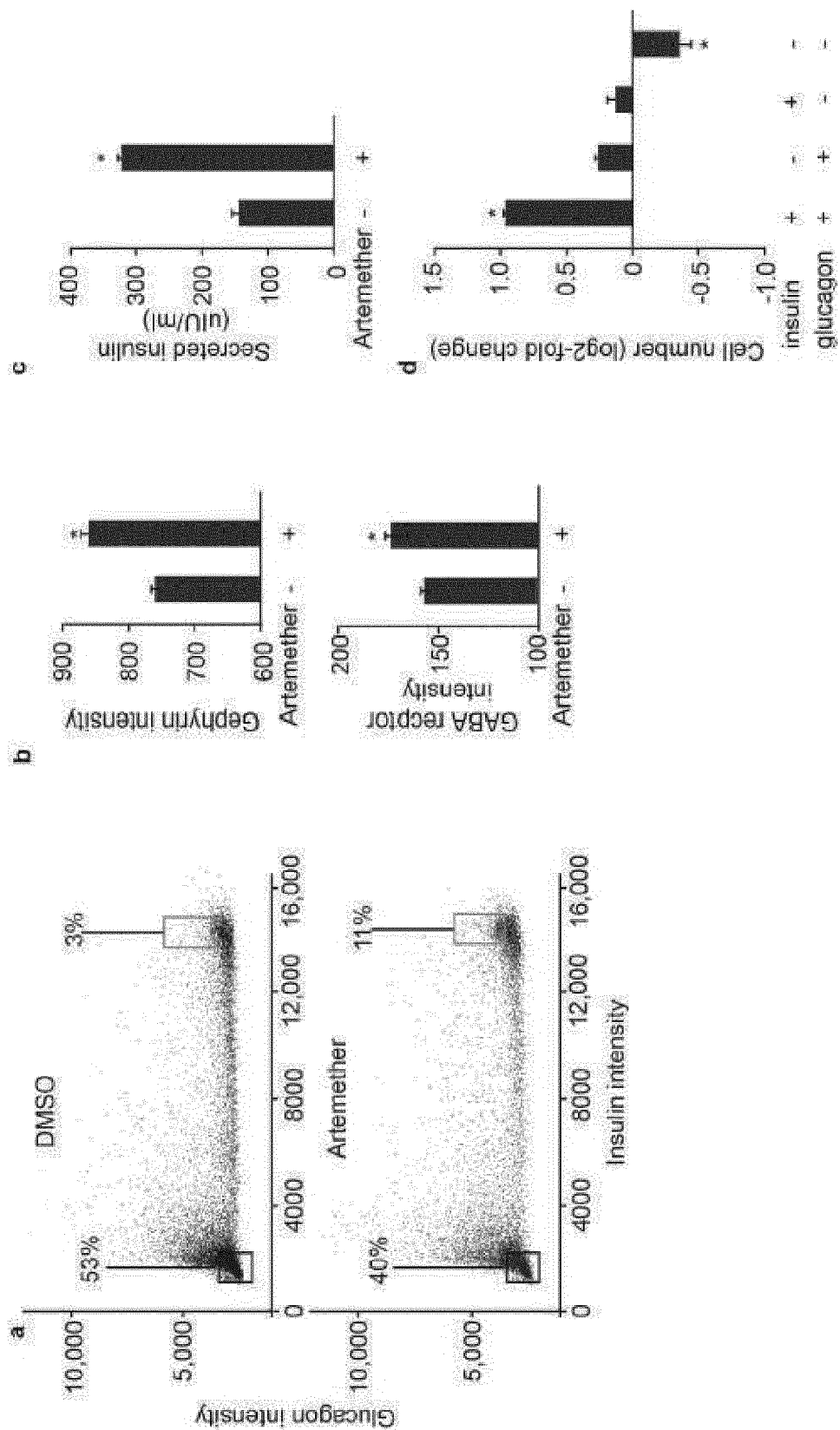

FIG. 6. Artemether induces cell type changes in human pancreatic islets. a. Immunofluorescence staining for insulin and glucagon in human islets with Artemether and control DMSO treatment for 72 hours. b. Quantification of gephyrin and GABA receptor abundance measured by immunofluorescence staining of human islets after 72 h treatment with Artemether and control DMSO. c. Glucose-stimulated insulin secretion measured by ELISA of supernatants from human islets after 72 h treatment with Artemether and control DMSO. d. Quantification of insulin/glucagon double-positive cells in human pancreatic islets.

FIG. 7: Primer sequences

DETAILED DESCRIPTION

The term "active agent" is herein understood in the following way. The active agent as described herein for medical use is particularly a small molecule or any suitable peptide, including polypeptides, proteins, including fragments of proteins, such as protein domains, in particular antibodies and antibody fragments or antibody domains, alternative scaffold binders, aptamers and nucleic acids.

For example, an active agent may be a molecule that may be synthesised by the techniques of organic chemistry, or by techniques of molecular biology or biochemistry, and is preferably a small molecule, which may be of less than 5000 Daltons and which may be water-soluble. An active agent as described herein may be an artemisinin compound and/or particularly exhibit features of selective interaction with gephyrin, e.g. similar to the agonistic activity of the artemisinin compounds of the invention.

The term "administration" as used herein shall include routes of introducing an active agent, such as an artemisinin compound or a candidate agent of the invention to a subject in need thereof to perform their intended function. Examples of routes of administration that may be used include oral administration. The agent can also be administered by any other convenient route, for example, by continuous infusion or bolus injection, by absorption through epithelial or mucocutaneous linings (e.g., oral, rectal, vaginal, and intestinal mucosa, etc.) and can be administered together with another therapeutic agent. Administration can be systemic or local. Various known delivery systems, including encapsulation in liposomes, microparticles, microcapsules, and capsules, can be used. Specific delivery systems employ patches for topical, transdermal or mucosal delivery, or implants. Specifically preferred are slow-release preparations or formulations and delivery systems to provide for the long-acting treatment.

Methods of administration of the active agent of this invention include, but are not limited to, intradermal, intramuscular, intraperitoneal, intravenous, subcutaneous, intranasal, epidural, oral, sublingual, intracerebral, intravaginal, transdermal, rectal, by inhalation, or topical. The active agent can be administered alone, or in combination or conjunction with either another agent or any other therapeutic treatment used in the indication, e.g. used to treat diabetes patients. The active agent can be administered prior to the administration of the other agent, simultaneously with the agent, or after the administration of the agent. Furthermore, the active agent of the invention can also be administered in a pro-drug form which is converted into its active metabolite, or more active metabolite in vivo. An alternative delivery system provide for the active agent associated with or bound to a carrier molecule, which is e.g. targeting a specific site of action. Exemplary delivery systems employ artemisinin compounds which are attached to iron-binding molecules and cell receptor-targeting molecules for selective delivery of a therapeutically effective amount into target disease cells, such carrier molecules for targeted delivery. Further examples refer to delivery of conjugates comprising at least two artemisinin compounds, or conjugates with other agents, including e.g. (pro)hormones or peptides, such as glucagon-like peptide 1 (GLP-1).

The term "inhibitor" in relation to BTBD9 activity as used herein shall specifically refer to a compound or an agent capable of combining with (e.g., binding to, interacting with) BTBD9 to initiate pharmacological actions, in particular to increase the level and/or activity of gephyrin. The agonistic activity of a test agent is specifically proven by any of the exemplary assays as described herein.

The term "agonist" in relation to gephyrin or gephyrin activity as used herein shall specifically refer to a compound or an agent capable of combining with (e.g., binding to, interacting with) gephyrin to initiate pharmacological actions, e.g. directly agonizing the gephyrin level or activity, or indirectly increasing the level or activity of gephyrin by inhibiting any antagonist, such as BTBD9. The agonistic activity of a test agent is specifically proven by any of the exemplary assays as described herein.

The term "artemisinin compound" as used herein shall specifically refer to artemisinin and artemisinin derivatives.

Artemisinin ((3R,5aS,6R,8aS,9R,12S,12aR)-octahydro-3,6,9-trimethyl-3,12-epoxy-12H-pyrano[4,3-j]-1,2-benzodioxepin-10(3H)-one) contains a 1,2,4-trioxane ring structure, and *Artemisia annua* and related *Artemisia* species are known to be the only natural source. It has the following structure:

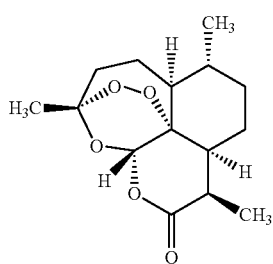 [SMILES: C[C@@H]1CC[C@H]2[C@@H](C)C(=O)O[C@@H]3O[C@]4(C)CC[C@@H]1[C@]32OO4]

Artemisinin derivatives specifically are understood as endoperoxides with a variety of residues, such as described in formula I herein. Exemplary compounds are selected from the group consisting of artelinic acid, artemether, artemotil (also referred to as arteether, β-arteether), artenimol (also referred to as dihydroartemisinin, β-dihydroartemisinin) and artesunate, or a pharmaceutically acceptable salt thereof, or derivatives or simplified analogs thereof.

Besides natural artemisinin compounds, semisynthetic or synthetic derivatives may be used, e.g. with improved solubility or bioavailability. Specifically, synthetic compounds with a similar trioxolane structure, such as arterolane, may also be used.

Specific derivatives include artemisone, dihydroartemisinin hemisuccinate, dihydrodroartemisinin succinate, dihydro-artemisinin glucuronide, sodium artesunate, stabilized forms of artesunate, stabilized forms of sodium artesunate, dihydroartemisitene dimers, 11-aza-artemisinin derivatives, amino-functionalized 1,2,4-trioxanes, artemisinin endoperoxides, deoxy-artemisinins, spiro and dispiro 1,2,4-trioxolane, mixed steroidal 1,2,4,5-tetraoxane compounds, substituted 1,2,4-trioxanes, *Artemisia annua* extracts or fractions of such extracts, trioxane derivatives based on artemisinin, seco-acrtemisinins, trioxane dimer compounds, conjugates of artelinic acid arteethers from dihydroartemisinin, artemisinine or artemisinene derivatives, C-10 carbon substituted artemisinin-like trioxane compounds, water-soluble trioxanes alpha arteether, artemisinin dimers, (+)-deoxoarteminisinin and analogs of (+)-deoxoartemisinin, and 10-substituted derivatives of dihydroartemisinin, as well as its salts or other derivatives thereof as known to one of skill in the art.

Specific derivatives may be obtained by dimerization or oligomerization, with or without using a linker, conjugation to other moieties, such as peptides, carriers or delivery agents, including receptor targeting molecules, combination with chelators that bind metal ions.

The term "diabetes" as used herein is specifically understood as a disease or disease disorder associated with Diabetes mellitus, irrespective of the genesis, specifically including diabetes Type I and Type II, C-peptide negative and positive diabetes, and associated disorders, including diabetic ketoacetosis, hyperglycemic hyperosmolar state, diabetic cardiomyopathy, diabetic nephropathy, diabetic encephalopathy, diabetic neuropathy, diabetic retinopathy, coronary artery disease, peripheral vascular disease, diabete myonecrosis, stroke, diabetic coma, and obesity.

Type I diabetes mellitus (also called juvenile diabetes) is a form of diabetes mellitus that results from the autoimmune destruction of the insulin-producing beta cells in the pancreas. Type II diabetes mellitus, which has both insulin-dependent and non-insulin-dependent types, typically appears later in a person's life as a result of genetic predisposition, improper diet, lack of exercise, or a combination thereof. Both forms of diabetes mellitus alter the body's ability to take up and metabolize blood glucose, leading to elevated levels of blood glucose. Chronically high levels of blood glucose may increase the risk for diabetes associated disorders, such as long-term vascular complications, e.g. coronary disease, heart attack, stroke, heart failure, kidney failure, blindness, erectile dysfunction, neuropathy (loss of sensation, especially in the feet), gangrene, and gastroparesis (slowed emptying of the stomach). Improper blood glucose control also increases the risk of short-term complications after surgery, such as poor wound healing.

The connecting peptide, or C-peptide, is a short 31-amino-acid protein that connects insulin's A-chain to its B-chain in the proinsulin molecule. Newly diagnosed diabetes patients often get their C-peptide levels measured as a means of distinguishing Type I diabetes and Type II diabetes.

Specific embodiments of the invention refer to treatment of diabetes, in particular diabetes type I or II, or C-peptide negative diabetes, or a disorder associated with an increased blood glucose level, e.g. including metabolic and insulin resistance disorders, such as any of the diabetes associated disorders as mentioned above or obesity in a patient suffering from diabetes or the respective disorder. Such anti-diabetes treatment specifically employs a pharmaceutical preparation of any of the artemisinin compounds of the invention or any other gephyrin agonist, specifically by a regimen of a gephyrin agonist exhibiting and formulated for sustained release and slow uptake to the patient's circulation when administered.

The term "lead" with respect to an active agent or a candidate agent is well known in the art, and shall refer to the meaning that an agent was selected for developing a pharmaceutical product, because its potential was proven by some assays, however, it would need to be further characterized by further tests and (preclinical or clinical) investigations to confirm its suitability to be used as a drug.

Test agents are typically characterized by appropriate test systems whether they are suitable used as an active agent for medical use.

Typically, if the candidate agent inhibits BTBD9 or interacts with gephyrin, such as to agonize its activity, or causes increased insulin expression by a pancreatic cell, e.g. as determined in a test system further described herein as compared to the activity or expression in the absence of the candidate agent, that candidate agent is characterized as a "lead candidate agent". Further, the lead candidate agent may be validated using an assay capable of demonstrating advantageous activities and properties to determine its potential to be used as a therapeutically active agent.

Such tests may be qualitatitive, quantitative or semi-quantitative.

The term "subject" as used herein shall refer to a warm-blooded mammalian, particularly a human being or a non-human mammalian animal, including dogs, cats, apes, pigs, sheep, and horses. In particular, the medical use of the invention or the respective method of treatment applies to a subject in need of prophylaxis or treatment of a disease condition (which includes a disease or disorder associated with such disease). The subject may be a patient suffering from disease, including early stage or late stage disease. The term "patient" includes human and other mammalian subjects that receive either prophylactic or therapeutic treatment. The term "treatment" is thus meant to include both prophylactic and therapeutic treatment.

A subject is e.g. treated for prophylaxis or therapy of diabetes or disorders associated with diabetes. Thus, specific embodiments refer to treatment of patients suffering from diabetes.

The term "pharmaceutically acceptable" as used herein refers to, for example, compounds, materials, compositions, and/or dosage forms which are suitable for use in contact with or in human beings and animals without excessive toxicity, irritation, allergic response, or other problems or complications, commensurate with a reasonable benefit/risk ratio.

The active agent of the invention may e.g. be formulated in an effective amount with a pharmaceutically acceptable carrier or diluent. Pharmaceutically acceptable carriers generally include any and all suitable solvents, dispersion media, coatings, antibacterial and antifungal agents, isotonic and absorption delaying agents, and the like that are physiologically compatible with an active agent or related composition or combination provided by the invention. Further examples of pharmaceutically acceptable carriers include sterile water, saline, phosphate buffered saline, dextrose, glycerol, ethanol, and the like, as well as combinations of any thereof.

In one such aspect, an active agent can be combined with one or more carriers appropriate for a desired route of administration, active agents may be, e.g. admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tableted or encapsulated for conventional administration.

Examplary formulations as used for parenteral administration include subcutaneous, intramuscular or intravenous injection as, for example, a sterile solution or suspension. Formulations for topical application include a number of forms such as creams or ointments, patches, pastes and gels.

Preferred pharmaceutically-acceptable carriers include vehicles, like sugars, such as lactose, glucose and sucrose, starches, such as corn starch and potato starch, cellulose and its derivatives, such as sodium carboxymethyl cellulose, ethyl cellulose and cellulose acetate, or polyols, such as glycerin, sorbitol, mannitol and polyethylene glycol, or other diluents and excipients known in the art to be employed in pharmaceutical formulations. Suitable examples of liquid carriers for oral and parenteral administration include water, particular containing additives as above, e.g. cellulose derivatives, including sodium carboxymethyl cellulose solution, alcohols including monohydric alcohols and polyhydric alcohols and their derivatives, and oils. The physiologically acceptable excipients can be saline, gelatin, starch, talc, keratin, colloidal silica, urea and the like. In addition, auxiliary, stabilizing, thickening, lubricating, and coloring agents can be used.

The active agent(s) may also be formulated so as to provide sustained or controlled release of the active ingredient therein using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. The active agent can also be in micro-encapsulated form, with one or more of the above-described excipients.

For example, an effective amount is provided in a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, slow-release formulation pharmaceutical compositions are suitable for mucosal, subcutaneous bolus or implants, topical or oral administration to a subject, including tablets, lozenges, buccal forms, troches, aqueous or oily suspensions or solutions, granules, powders, pastes, emulsions, capsules, syrups elixirs, liposomal formulations, drug-polymer conjugates or nanoparticle formulations.

Additional pharmaceutically acceptable carriers and pharmaceutical compositions are known in the art and described in, e.g. REMINGTON'S PHARMACEUTICAL SCIENCES.

Specific pharmaceutical compositions are contemplated wherein an active agents, such as an artemisinin compound of the present invention and one or more pharmaceutically acceptable carriers and optionally one or more further therapeutically active agents are formulated. Stable formulations of the active agent are prepared for storage by mixing said agent having the desired degree of purity with optional pharmaceutically acceptable carriers, excipients or stabilizers, in the form of lyophilized formulations or aqueous solutions.

The term "screening" as used herein shall refer to identification of a candidate agent which specifically passes a screening test, e.g. to inhibit BTBD9 activity or agonise gephyrin activity, which is indicative that the candidate agent is a potential therapeutic active agent that may be useful in the treatment of a disease or disorder, such as diabetes. For example, the screening assays described herein are useful for identifying a lead candidate agent from a plurality of test agents. According to a specific aspect, a direct binding assay is provided which determines the interaction of a test agent with gephyrin.

The capability of a test agent to bind to or interact with BTBD9 or gephyrin may be measured by any method of detecting/measuring a protein/protein interaction or other compound/protein interaction. Specific methods of identifying an agent that are capable of binding to BTBD9 or gephyrin are ones where BTBD9 or gephyrin is exposed to the agent and any binding of the agent to gephyrin is detected and/or measured. The binding constant for the binding of the agent to BTBD9 or gephyrin may be determined. Suitable methods for detecting and/or measuring (quantifying) the binding of an agent to BTBD9 or gephyrin are well known in the art and may be performed, for example, using co-purification, ELISA, co-immunoprecipitation, isothermal titration calorimitry, differential scanning fluorimetry (Thermofluor), fluorescence polarization, fluorescence resonance energy transfer, scintillation proximity assays and surface plasmon resonance methods, and specifically a method capable of high throughput operation, for example a chip-based method.

Further methods of detecting polypeptide/polypeptide interactions include ultrafiltration with ion spray mass spectroscopy/HPLC methods or other physical and analytical methods. Fluorescence Energy Resonance Transfer (FRET) methods, for example, may be used as well, in which binding of two fluorescent labelled entities may be measured by measuring the interaction of the fluorescent labels when in close proximity to each other.

According to a specific aspect, the activity of BTBD9 is determined by measuring the binding of BTBD9 to CUL3 by coimmunoprecipitation using an antibody against BTBD9 and detecting the amount of bound CUL3 with primary antibody specifically recognizing CUL3, either directly labeled with a fluorophore or other appropriate signal-generating molecule (e.g. horseradish peroxidase, luciferase) or indirect detection with a similarly labeled secondary antibody. Alternatively, the immunoprecipitation is performed with an antibody against CUL3 and detecting the amount of bound BTBD9 with primary antibody specifically recognizing BTBD9, either directly labeled with a fluorophore or other appropriate signal-generating molecule (e.g. horseradish peroxidase, luciferase) or indirect detection with a similarly labeled secondary antibody. Alternative detection methods include immunochemical or mass-spectrometric quantification of to same binding interaction. A further alternative method includes the direct labeling of gephyrin with green fluorescent protein or another cellularly encoded fluorophore or otherwise easily detectable tag by knocking-in the coding sequence into the endogenous gephyrin locus, the labeling of CUL3 with another fluorophore and detection of the interaction by Förster resonance energy transfer. A further alternative method includes the quantification of the interaction of BTBD9 and CUL3 by surface plasmon resonance, isothermal calorimetry or equivalent biophysical methods.

The BTBD9 binder (e.g. the artemisinin compounds as described herein) would specifically inhibit the interaction between BTBD9 and the E3 ubiquitin ligase CUL3, preventing the ubiquitination and subsequent degradation of gephyrin. Thereby, these compounds act as BTBD9 inhibitors, but indirectly also agonists of gephyrin as they result in increased gephyrin protein levels.

According to another specific aspect, the level or clustering of gephyrin is determined by measuring the amount and intracellular location of gephyrin in an immunofluorescence assay using a primary antibody specifically recognizing gephyrin, either directly labeled with a fluorophore or other appropriate signal-generating molecule (e.g. horseradish peroxidase, luciferase) or indirect detection with a similarly labeled secondary antibody. Alternative detection methods include immunochemical or mass-spectrometric quantification of gephyrin in lysates generated from whole cells or specific membrane-enriched fractions. A further alternative method includes the direct labeling of gephyrin with green fluorescent protein or another cellularly encoded fluorophore or otherwise easily detectable tag by knocking-in the coding sequence into the endogenous gephyrin locus.

According to another specific aspect, the increase, enhancement, stimulation, or promotion of binding gephyrin to GABAR is determined as follows: Using co-immunoprecipitation, anti-gephyrin antibodies are used to immunoprecipitate gephyrin, and associated GABA receptor is measured by Western blot or ELISA. Alternative methods include the use for tagged proteins and detection by Fluorescence Resonance Energy Transfer FRET or alternative assays e.g. LUMIERE.

According to another specific aspect, the increase of gephyrin-mediated signaling of the GABAR is determined as follows: Directly by measuring the resuling influx of chloride ions into the cell using e.g. chloride sensitive dyes e.g. N-(6-methoxyquinolyl)-acetoethyl ester (MQAE) or indirectly by electrophysiological measurement of the cell's membrane potential or the resulting intracellular changes in gene expression.

Exemplary assays to test gephyrin agonist activity of a test agent are based on the determination of its activity to
  i) increase the thermal stability of BTBD9; and/or
  ii) inhibit the binding of BTBD9 to CUL3; and/or
  iii) increase the level or clustering of gephyrin; and/or
  iv) increase, enhances, stimulates, or promotes binding of gephyrin to GABAR; and/or
  v) to increase gephyrin-mediated signaling of the GABAR.

Such assays are e.g. direct binding assays, immunofluorescence staining assays, immunochemical methods, biophysical methods or electrophysiological methods.

For example, a suitable binding assay is further described in the examples below.

Specific test agents may be screened for their potential to be used for treatment of diabetes. Therefore, specific screening tests may be used which are cell-based assays. Exemplary assays to test the anti-diabetic activity of a test agent are based on its activity to express insulin in a pancreatic cell, particularly, an alpha-cell or a beta-cell that overexpresses ARX, to determine if the test agent
  i) increases insulin expression by said cell; and/or
  ii) represses ARX in said cell; and/or
  iii) inhibits the binding of BTBD9 to CUL3; and/or
  iv) increases the level or clustering of gephyrin; and/or
  v) increases gephyrin-mediated signaling of the GABAR.

For example, a suitable insulin expression assay is further described in the examples below.

Optionally, the screening method may include repeating the method steps of a test, e.g. in a high throughput screen. Thereby a plurality of candidate agents may be tested to identify a lead candidate agent for medical use.

For example, combinatorial chemical libraries or chemical libraries, including collections of diverse chemical compounds generated by either chemical synthesis or biological synthesis, for example, linear combinatorial chemical libraries such as polypeptide or peptide libraries may be used as a source of test agents. Such library members, chemical species or subclasses, may be selected that display a desired characteristic activity, for example, capable of agonistically binding to gephyrin, or increase the expression of insulin in pancreatic cells (in an in vitro or ex vivo assay).

It is appreciated that the identification of an agent that binds to or interacts with BTBD9 or gephyrin may be an initial step in a drug screening pathway, and the identified agent may be further characterized and selected e.g. for the ability to agonise gephyrin activity. Therefore, the method of the invention may further include assaying a lead candidate agent in an activity assay to determine whether the lead candidate agent would qualify for a therapeutically active agent.

The term "effective amount" as used herein is intended to mean that amount of a compound that is sufficient to treat, prevent or inhibit such diseases or disorder. In the context of disease, therapeutically effective amounts of an active agent as described herein are specifically used to prevent, treat, modulate, attenuate, reverse, or affect a disease or condition that benefits from an interaction of the active agent with cellular components or molecules, e.g. including interactions with BTBD9 or gephyrin, and specifically diabetes. The term specifically includes both, therapeutically and prophylactically effective amounts.

The term "prophylactically effective amount" specifically refers to an amount of an active agent, which is effective, upon single or multiple dose administration to the patient, in preventing or treating a disease or disorder.

The amount of the active agent that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

A therapeutically effective amount of an active agent which is an artemisinin compound as described herein, such as provided to a human patient in need thereof, may specifically be in the range of 0.01-2000 mg/day, preferably 0.1-500 mg/day, in a single dose or multiple doses. Specific embodiments refer to slow-release formulations or devices, which may be advantageously employed to administer the active agent over a prolonged period of time, such as for treatment of chronic disease, e.g. a treatment over at least 2 weeks, at least 3 weeks or at least 4 weeks. In a specific embodiment, a slow release formulation provides for a blood level of an artemisinin compound, which is in the range of 0.01-500 mg/day constantly over the entire treatment period. In another specific embodiment, such concentrations are reached intermittently, e.g. in a repeated regimen of 1 week on-treatment, 1 off-treatment. In another embodiment, the specific formulation results in the selective enrichment for the active agent in the pancreas or pancreatic islets in the absence of detectable blood levels.

A treatment or prevention regime of a subject with a therapeutically effective amount of the active substance of the present invention may consist of a single administration, or alternatively comprise a series of applications. For example, the active agent may be administered at least once a year, at least once a half-year or at least once a month. However, in another embodiment, the active agent may be administered to the subject from about one time per week to about a daily administration for a given treatment. The length of the treatment period depends on a variety of factors, such as the severity of the disease, either acute or chronic disease, the age of the patient, the concentration and the activity of the active agent. It will also be appreciated that the effective dosage used for the treatment or prophylaxis may increase or decrease over the course of a particular treatment or prophylaxis regime. Changes in dosage may result and become apparent by standard diagnostic assays known in the art. In some instances, chronic administration may be required.

The biological properties of the artemisinin compound or the active agent and pharmaceutical preparations of the invention may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, non-obese diabetic (NOD) mice, xenograft mice, and transgenic mice (including knockins and knockouts). Such experimentation may provide meaningful data for determination of the potential of an active agent to be used as a therapeutic or as a prophylactic. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the subject agent or composition. Tests in humans are ultimately required for approval as drugs, and thus of course these experiments are contemplated. Thus, the active agent and respective pharmaceutical compositions of the present invention may be tested in humans to determine their therapeutic or prophylactic efficacy, toxicity, immunogenicity, pharmacokinetics, and/or other clinical properties.

According to the invention preferred active agents, such as small molecule artemisinin compounds are those commercially available compounds that have been used in anti-malarial or anti-viral therapy for a different purpose, like Arteether; Artemotil; Artemether; Artemisone; Artesunate; Artemisinin; Artemisitene; Artelinic acid; 9-epi-artemisinin; Dihydroartemisinin; Dihydro Artemisinin Dimer; Dihydroartemisinin Glucuronide; 3,6,9-trimethyldecahydro-3,12-epoxy[1,2]dioxepino[4,3-i]isochromen-10-ol; (3R,5aS,6R,8aS,9R,12R,12aR)-Decahydro-3,6,9-trimethyl-3,12-epoxy-12H-pyrano[4; 3,12-Epoxy-12H-pyrano[4,3-j]-1,2-benzadioxepin-10(3H)-one, octahydro-3,6,9-trimethyl-; (3R,5aS,6R,8aS,9R,10S,12R,12aR)-3,6,9-trimethyldecahydro-3H-3,12-epoxy[1,2]dioxepino[4,3-i]isochromen-10-ol; 3,12-Epoxy-12H-pyrano[4,3-j]-1,2-benzodioxepin-10(3H)-one, octahydro-3,6,9-trimethyl-, (3R,5aS,6R,8R,12S,12aR)-; 3,12-Epoxy-12H-pyrano[4,3-j]-1,2-benzodioxepin-10-al, decahydro-3,6,9-trimethyl-, (3S,5aS,6R,8aS,9R,10S,12R,12aR)-; (3R,5aS,6R,8aS,9R,10S,12R,12aR)-Decahydro-10-ethoxy-3,6,9-trimethyl-3,12-epoxy-12H-pyrano[4,3-j]-1,2-benzodioxepine; 3,12-Epoxy-12H-pyrano[4,3-j]-1,2-benzodiaxepin, 10-fluorodecahydro-3,6,9-trimethyl-, (3R,5aS,6R,8aS9R,10R,12S,12aR)-; 3,12-Epoxy-12H-pyrano[4,3-j]-1,2-benzodioxepin-10-ol, decahydro-10-d-3,6,9-trimethyl-, (3R,5aS,6R,8aS,9R,10S,12R,12aR)-(9Cl); 4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanoic acid; Butanedioic acid, 1-[(3R,5aS,6R,8aS,9R,10R,12R,12aR)-decahydro-3,6,9-trimethyl-3,12-epoxy-12H-pyrano[4,3-j]-1,2-benzodioxepin-10-yl] ester; (3R,5aS,6R,8aS,9R,10S,12R,12aR)-3,6,9-trimethyldecahydro-3H-3,12-epoxy[1,2]dioxepino[4,3-i]isochromen-10-yl 4-(isobutylamino)-4-oxobutanoate; 2,5-dioxopyrrolidin-1-yl ((3R,5aS,6R,8aS,9R,10S,12R,12aR)-3,6,9-trimethyldecahydro-3H-3,12-epoxy[1,2]dioxepino[4,3-i]isochromen-10-yl) succinate; N,N-Dimethyl-N-[2-[(3R,5aS,6R,8aS,9R,10S,12R,12aR)-3,6,9-trimethylperhydro-3,12-epoxypyrano[4,3-j]-1,2-benzodioxepin-10-yloxy]ethyl]amine oxalate; (3R,5aS,6R,8aS,9R,10S,12R,12aR)-3,6,9-trimethyldecahydro-3H-3,12-epoxy[1,2]dioxepino[4,3-i]isochromen-10-yl 4-oxo-4-((1-phenylethyl)amino)butanoate; (3R,5aS,6R,8aS,9R,10S,12R,12aR)-3,6,9-trimethyldecahydro-3H-3,12-epoxy[1,2]dioxepino[4,3-i]isochromen-10-yl 4-((4-methoxybenzyl)amino)-4-oxobutanoate; 6-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido) hexanoic acid; (3R,5aS,6R,8aS,9R,10S,12R,12aR)-3,6,9-trimethyldecahydro-3H-3,12-epoxy[1,2]dioxepino[4,3-i]isochromen-10-yl 4-((cyclohexylmethyl)amino)-4-oxobutanoate; (3R,5aS,6R,8aS,9R,10S,12R,12aR)-3,6,9-trimethyldecahydro-3H-3,12-epoxy[1,2]dioxepino[4,3-i]isochromen-10-yl 4-((furan-2-ylmethyl)amino)-4-oxobutanoate; 2-(4-oxo-4-(((3R,5aS,6R,8a5,9R,10S,12R,12aR)-3,6,9-trimethyldecahydro-3H-3,12-epoxy[1,2]dioxepino[4,3-i]isochromen-10-yl)oxy)butanamido) propanoic acid; (3R,5aS6R,8aS,9R,10S,12R,12aR)-3,6,9-trimethyldecahydro-3H-3,12-epoxy[1,2]dioxepino[4,3-i]isochromen-10-yl 4-((4-fluorophenethyl)amino)-4-oxobutanoate; (3R,5aS,6R,8aS,9R,10S,12R,12aR)-3,6,9-trimethyldecahydro-3H-3,12-epoxy[1,2]dioxepino[4,3-i]isochromen-10-yl 4-((2,2-dimethoxyethyl)amino)-4-oxobutanoate; (3R,5aS,6R,8aS,9R,10S,12R,12aR)-3,6,9-trimethyldecahydro-3H-3,12-epoxy[1,2]dioxepino[4,3-i]isochromen-10-yl 4-((4-hydroxyphenethyl)amino)-4- oxobutanoate; (3R,5aS,6R,8aS,9R,10S,12R,12aR)-3,6,9-trimethyldecahydro-3H-3,12-epoxy[1,2]dioxepino[4,3-i]isochromen-10-yl 4-((4-methoxyphenethyl)amino)-4-oxobutanoate; (3R,5aS,6R,8aS,9R,10S,12R,12aR)-3,6,9-trimethyldecahydro-3H-3,12-epoxy[1,2]dioxepino[4,3-i]isochromen-10-yl 4-oxo-4-((pyridin-4-ylmethyl)amino)butanoate; 3-hydroxy-2-(4-(4-oxo-4-(((5aS,6R,12S)-3,6,9-trimethyldecahydro-3H-3,12-epoxy[1,2]dioxepino[4,3-i]isochromen-10-yl)oxy)butanamido)butanamido)butanoic acid; (3R,5aS,6R,8aS,9R,10S,12R,12aR)-3,6,9-trimethyldecahydro-3H-3,12-epoxy[1,2]dioxepino[4,3-i]isochromen-10-yl 4-((2-(1H-indol-3-yl)ethyl)amino)-4-oxobutanoate; 4-((4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)methyl)benzoic acid; 4-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)-3-phenylbutanoic acid; (3R,5aS,6R,8aS,9R,10S,12R,12aR)-3,6,9-trimethyldecahydro-3H-3,12-epoxy[1,2]dioxepino[4,3-i]isochromen-10-yl 4-((2-(1H-imidazol-5-yl)ethyl)amino)-4-oxobutanoate; (5aS,6R,12S)-3,6,9-trimethyldecahydro-3H-3,12-epoxy[1,2]dioxepino[4,3-i]isochromen-10-yl 4-((4-((2,5-dioxopyrrolidin-1-yl)oxy)-4-oxobutyl)amino)-4-oxobutanoate; (3R,5aS,6R,8aS,9R,10S,12R,12aR)-3,6,9-trimethyldecahydro-3H-3,12-epoxy[1,2]dioxepino[4,3-i]isochromen-10-yl 4-oxo-4-(((tetrahydrofuran-2-yl)methyl)amino)butanoate; 3-(1H-indol-3-yl)-2-(4-(4-oxo-4-(((5aS,6R,12S)-3,6,9-trimethyldecahydro-3H-3,12-epoxy[1,2]dioxepino[4,3-i]isochromen-10-yl)oxy)butanamido)butanamido)propanoic acid; 4-(methylthio)-2-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)butanoic acid; 5-amino-5-oxo-2-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)pentanoic acid; 2-((S)-4-methyl-2-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)pentanamido)acetic acid; (S)-3-methyl-2-(4-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)butanamido)butanoic acid; Butanoic acid, 4-[[2-(3,4-dihydroxyphenyl)ethyl]amino]-4-oxo-, (3R,5aS,6R,8aS,9R,10S,12R,12aR)-decahydro-3,6,9-trimethyl-3,12-epoxy-12H-pyrano[4,3-j]-1,2-benzodioxepin-10-yl ester; (3R,5aS,6R,8aS,9R,10S,12R,12aR)-3,6,9-trimethyldecahydro-3H-3,12-epoxy[1,2]dioxepino[4,3-i]isochromen-10-yl 4-(((S)-3-(1H-indol-3-yl)-1-methoxy-1-oxopropan-2-yl)amino)-4-oxobutanoate; (S)-2-((S)-4-methyl-2-(4-oxo-4-(((3R,5aS,6R,8aS,9R,10S,12R,12aR)-3,6,9-trimethyldecahydro-3H,3,12-epoxy[1,2]dioxepino[4,3-i]isochromen-10-yl)oxy)butanamido)pentanamido)propanoicacid; (S)-2-((S)-4-methyl-2-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)pentanamido)pentanedioic acid; (S)-3-methyl-2-((S)-4-methyl-2-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)pentanamido)butanoic acid; (S)-2-((S)-4-methyl-2-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)pentanamido)-3-phenylpropanoic acid; (S)-4-methyl-2-((S)-4-methyl-2-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)pentanamido)pentanoic acid; 3-(2,2-dimethyltetrahydro-2H-pyran-4-yl)-3-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)propanoic acid; (3R,5aS,6R,8aS,9R,10S,12R,12aR)-3,6,9-trimethyldecahydro-3H-3,12-epoxy[1,2]dioxepino[4,3-i]isochromen-10-yl 4-(((S)-1-((4-hydroxyphenethyl)amino)-4-methyl-1-oxopentan-2-yl)amino)-4-oxobutanoate; (R)-3-mercapto-2-((S)-4-methyl-2-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)pentanamido)propanoic acid; (2S,3R)-3-methyl-2-((S)-4-methyl-2-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)pentanamido)pentanoic acid; (S)-3-(1H-indol-3-yl)-2-((S)-4-methyl-2-(4-oxo-4-(((3R,5aS,6R,8aS,9R,10S,12R,12aR)-3,6,9-trimethyldecahydro-3H-3,12-epoxy[1,2]dioxepino[4,3-i]isochromen-10-yl)oxy)butanamido)pentanamido)propanoic acid; (3R,5aS,6R,8aS,9R,10S,12R,12aR)-3,6,9-trimethyldecahydro-3H-3,12-epoxy[1,2]dioxepino[4,3-i]isochromen-10-yl 4-(((S)-1-(((S)-1-ethoxy-3-(4-hydroxyphenyl)-1-oxopropan-2-yl)amino)-4-methyl-1-oxopentan-2-yl)amino)-4-oxobutanoate; (3R,5aS,6R,8aS,9R,10S,12R,12aR)-3,6,9-trimethyldecahydro-3H-3,12-epoxy[1,2]dioxepino[4,3-i]isochromen-10-yl 4-(((S)-1-(((S)-3-(1H-indol-3-yl)-1-methoxy-1-oxopropan-2-yl)amino)-4-methyl-1-oxopentan-2-yl)amino)-4-oxobutanoate; or functional derivatives thereof with proven anti-diabetes activity.

Further functional derivatives of artemisinin or any of the specific artemisinin compounds as described herein may be synthesized or can be identified by appropriate screening technology employing a test for BTBD9 binding, gephyrin binding or gephyrin agonistic activity or BTBD9 inhibitory activity.

Also preferred are active agents, which mimic the structure of an artemisinin compound or another gephyrin binding partner, or which are specific ligands of gephyrin, like agonistic antibodies or antibody fragments.

In one embodiment of the invention, the active agent is the only therapeutically active agent administered to a subject, e.g. as a disease modifying or preventing monotherapy.

In another embodiment, the active agent is combined with further active agents in a cocktail, e.g. combined in a mixture or kit of parts, such that the cocktail contains more than one therapeutically active agents administered to a subject, e.g. as a disease modifying or preventing combination therapy.

Specifically, the active agent may also be administered in combination with one or more other therapeutic or prophylactic agents, including but not limited to standard treatment for treating the same target indication, e.g. active agents for treating diabetes, including any of insulin, sulfonylureas, incretins, other secretagogues, glitazones, metformin, GLP-1 agonists or DPP4 inhibitors, glucosidease inhibitors, amylin analogs, SGLT2 inhibitors, gastric bypass surgery or pancreatic island transplantation.

In a combination therapy, the active agent may be administered as a mixture, or concomitantly with one or more other therapeutic regimens, e.g. either before, simultaneously or after concomitant therapy.

In certain embodiments, the methods of the invention include administering to a subject a therapeutically effective amount of an active agent which is an active agent, like an artemisinin compound or another BTBD9 inhibitor or gephyrin agonist of the invention in combination with another pharmaceutically active agent or conventional treatment methods. Examples of pharmaceutically active anti-diabetic compounds include insulin, sulfonylureas, other secretagogues, glitazones, metformin or other bioguanides, GLP-1 agonists or DPP4 inhibitors, other incretins, glucosidease inhibitors, amylin analogs, SGLT2 inhibitors, gastric bypass surgery or pancreatic islet transplantation. The present invention, further relates to kits comprising the active agent of the invention and drugs as used for combination therapy.

The active agent of the invention and the other pharmaceutically active compound may be administered to the subject in the same pharmaceutical composition or in different pharmaceutical compositions, e.g. at the same time or at different times.

The term "Moco deficiency" refers to disease in lack of active sulfite oxidase, xanthine dehydrogenase/oxidase, aldehyde oxidase or any further enzymes whose activity require the presence and enough level of Molybdenum cofactor, irrespective of genesis. The diagnosis of Moco deficiency includes, but is not limited to early seizures, low blood levels of uric acid, and high levels of sulphite, xanthine, and uric acid in urine.

The term "temporal lobe epilepsy" is used to describe the recurrent epilepsy originating from temporal lobe. The temporal lobe is a region of the cerebral cortex that is located beneath the lateral fissure on both cerebral hemispheres of the mammalian brain. The epilepsy is a disorder of the brain characterized by an enduring predisposition to generate epileptic seizures and by the neurobiologic, cognitive, psychological, and social consequences of this condition. The definition of epilepsy requires the occurrence of at least one epileptic seizure.

Moco deficiency is a inheritary disease with caused by mutation in MCOS1, MCOS2 or gephyrin, leading to absence xanthine dehydrogenase/oxidase and aldehyde oxidase activity (Reiss and Johnson, 2003). A few cases of Moco deficiency have been reported and only one patient was cured so far. Due to the facts that there are no approved therapies available for Moco deficient, artemether, because of its agonistic effect of artemether on gephyrin, has the potential to become the orphan drug for Moco deficiency.

Recent studies unveil the unique role of gephyrin in temporal lobe epilepsy. Low level of gephyrin was detected in temporal lobe epilepsy patients as well as experimental mouse model, and these might due to the unproper splicing of gephyrin mRNA (Forstera et al., 2010). Based on our study, artemether treatment can increase the stability of gephyrin in both mouse and human cells. These results show the possibility for artemether to be involved in the therapies against temporal lobe epilepsy.

In a further another aspect of the invention, a method is provided to identify an active agent suitable for anti-diabetic treatment. Functional assays involve the ex vivo use of pancreatic cells, e.g. pancreatic alpha-cells or pancreatic beta-cells that overexpresses ARX, to test if the test agent
  i) increases insulin expression by said cell; and/or
  ii) represses ARX in said cell; and/or
  iii) inhibits the binding of BTBD9 to CUL3; and/or
  iv) increases the level or clustering of gephyrin; and/or
  v) increases gephyrin-mediated signaling of the GABAR.

Methods to determine BTBD9 interaction or gephyrin interaction, e.g. gephyrin agonistic activity in vitro include co-purification, ELISA, co-immunoprecipitation, isothermal titration calorimtry, differential scanning fluorimetry (Thermofluor), fluorescence polarization, fluorescence resonance energy transfer, scintillation proximity assays and surface plasmon resonance methods, and specifically a method capable of high throughput operation, for example a chip-based method.

Compounds may as well be computer modeled into or on the BTBD9 or gephyrin crystal structure. Once potential modulating compounds are identified, the compounds may be screened using in vitro, in vivo, or ex vivo cellular assays. Compounds identified in this manner are useful as analogs of the preferred active agents of the invention.

The foregoing description will be more fully understood with reference to the following examples. Such examples are, however, merely representative of methods of practicing one or more embodiments of the present invention and should not be read as limiting the scope of invention.

EXAMPLE

Materials and Methods

Reagents

Antibodies used in this project are insulin (Sigma 18510), glucagon (Sigma G2654), Pax4 (R&D AF2614, Lot No. UZY0110121), Pax4 (Santa Cruz 98942, Lot No. H1610), Arx (R&D AF7068, Lot No. CFOM0211121), Myc (Cell Signaling Technology CST2276, Lot 19), Histone H2B (Cell Signaling Technology CST2934, Lot 1), Gephyrin (Abcam, ab25784), Gephyrin (Synaptic Systems, 147 111), Cul3 (Abcam, ab75851), Btbd9 (Abnova, H00114781-D01), Btbd9 (Abcam, ab174976). Artemether and primers were obtained from Sigma. The sequences of primers are indicated in FIG. 7. Cy-3-labeled donkey-α-guinea pig antibody from Jackson ImmunoResearch. All other fluorescently labeled antibodies were purchased from Life Technologies Corporation. All the HRP-labeled antibodies were purchased from Jackson Lab.

Cell Culture

Mouse pancreatic cell lines αTC1 (provided by Novo Nordisk) and βTC3 (provided by Novo Nordisk) were grown in low-glucose DMEM supplemented by 10% FBS, 50 U/mL penicillin and 50 μg/mL streptomycin. Mouse pancreatic cell lines Min6 (provided by Novo Nordisk) with Doxycycline inducible construct was grown in high-glucose DMEM supplemented by 15% Tet System Approved FBS (Clonetech 631106), 71 uM 2-mercaptoethanol, 50 U/mL penicillin and 50 ug/mL streptomycin. The cell culture for human islets followed established protocols (Walpita et al., 2012).

High-Through Put Screening

Compounds (50 nL) were transferred to black optical suitable 384-well plate (Corning 3712) from DMSO stock plates using acoustic transfer (Labcyte Inc.). Min6 cells (3000 cells per well) were plated in 50 ul media on top of the compounds. Three days after treatment, cells were fixed in 3.7% formaldehyde for ten minutes at room temperature. Following PBS washing, cells were fixed with cold pure methanol at −20° C. for 10 minutes, permeabilized by 1% Triton X-100 in PBS for 30 minutes and blocked by 3% BSA in PBS for 30 minutes. Twenty microliters of primary anti-insulin antibody, diluted in 1:2000 in 1.5% BSA, was added per well and incubated in 4° C. overnight. After washing with PBS twice, 20 μL Cy-3-labeled donkey-α-guinea pig antibody diluted in 1:1000 and 10 ug/mL Hoechst 3342 in PBS was added per well and incubated for 1 h. After two washes with PBS, plates were stored at 4° C. in the dark until analysis.

Images were taken by an automated microscope (Perkin Elmer Operetta) using a 20× objective. Images were exposed for 10 ms in Hoechst channel and 500 ms in Alexa Fluor 548 channel. Images were analyzed by the Harmony (Perkin Elmer) software. Nuclei were identified (Harmony Method C) and cytoplasm was defined based on the nuclei (Harmony Method C). In total 1152 wells were screened containing 280 compounds from a collection of clinical approved drugs with unique structure (CeMM, Vienna, Austria) in triplicates with control wells. Hits were selected based on the intensity of insulin in the Alexa Fluor 548 channel and cell numbers in the Hoechst channel.

RNA-Seq

After incubation with or without doxycycline for 24, 72, and 144 h, cells were lysed and RNA isolated using the RNeasy Mini Kit (Qiagen) according to the manufacturer's protocol. The library for RNA-seq was prepared with Ribozero Kit and Scriptseq v2 Kit (Epicenter) or by fully automatic robotic library preparation. The deep sequencing was done at the Biomedical Sequencing Facility at CeMM. The raw data was aligned and quantified by tophat and Bowtie 2.0.

RT-qPCR

After the RNA was isolated with RNeasy Mini Kit (Qiagen), it was reverse transcribed with random primers using the High Capacity cDNA Reverse Transcription Kit (Applied Biosystems). Quantitative PCR was performed with Power SYBR Green PCR Master Mix (Applied Biosystems) on Lightcycler 480 qPCR machine (Roche).

Western Blot

Whole cell extracts were generated by lysing cells in NP-40 buffer containing 150 mM sodium chloride, 1.0% NP-40 and 50 mM Tris, pH 8.0 supplemented by Protease Inhibitor Cocktail (Roche). The whole-cell lysate (30 μg) was loaded onto a SDSpolyacrylamide gel for electrophoresis at 30 mA per gel, and then transferred by electrophoresis to a nitrocellulose membrane (GE Healthcare Life Science). All the blots were incubated with the corresponding primary antibodies diluted in 1:1000 in 5% milk at 4° C. overnight and with HRP-labeled secondary antibodies (diluted 1:20000) for 1 h. The signals were detected using ECL Prime Western blotting Detection Reagent (Amersham).

Chemical Proteomics

NMR spectra were recorded on a Bruker Avance III 400 (Bruker, Billerica, Mass., U.S). Chemical shifts are given in ppm, and coupling constants are given in hertz. Mass spectra were recorded using a XeVo-UPLC-TQ-MS system (Waters, Milford, Mass., U.S.). Purification by flash column chromatography (FCC) was done using silica gel 60 (Merck, Darmstadt, Germany), MPLC was performed on a Biotage Isolera system (Biotage, Uppsala, Sweden). The purity of the synthesized compounds was determined and confirmed by UPLC analysis.

All synthesis chemicals were purchased from Sigma-Aldrich and used without further purification.

Drug-affinity matrices were prepared essentially as described previously (Huber et al, 2014). Briefly, ethylenediamine (2.7 μL, 40 μmol), ethanolamine (9.7 μL, 160 μmol), and triethylamine (15 μL, 108 μmol) were added to 500 μL NHS-activated Sepharose 4 Fast Flow beads (GE Healthcare Bio-Sciences AB, Uppsala, Sweden) and the reaction was put on a rotary shaker for 24 h. Beads were washed and resuspended in DMSO and NHS-activated artesunate (100 μL, 1.00 μmol) was added to the suspension, and the mixture was put on a rotary shaker for 24 h. Unreacted beads were blocked by addition of NHS-acetate (10 μmol) and triethylamine (25 μL, 180 μmol), followed by agitation on a rotary shaker for 24 h. After washing with DMSO and lysis buffer, beads were incubated with cell lysates.

Affinity chromatography and elution were performed in duplicate as reported previously (Huber et al, 2014), using 10 mg total cell lysate as protein input per replicate.

After elution, enriched proteins were reduced with dithiothreitol, cysteine residues alkylated by incubation with iodoacetamide and the samples digested with modified porcine trypsin (Promega, Madison, Wis.). Three percent (and multiples thereof) of the digested eluates were purified and concentrated by C18 reversed-phase material for subsequent duplicate analysis by gel-free one-dimensional liquid chromatography mass spectrometry (1D-LCMS). Details of the LCMS methodology are as previously described.

Peak extraction and conversion of RAW files into the MGF format for subsequent protein identification was performed with msconvert (ProteoWizard Library v2.1.2708). An initial database search was performed with broader mass tolerance to re-calibrate the mass lists for optimal final protein identification. For the initial protein database search, Mascot version 2.3.02 (Matrix Science Ltd., London, UK) was used. Error tolerances on the precursor and fragment ions were ±10 ppm and ±0.6 Da, respectively, and the database search limited to fully-tryptic peptides with maximum 1 missed cleavage, carbamidomethyl cysteine and methionine oxidation set as fixed and variable modifications, respectively. The Mascot peptide ion score threshold was set to 30, and at least 3 peptide identifications per protein were required. Searches were performed against the human UniProtKB/SwissProt database release 2012-05 including all protein isoforms.

The initial peptide identifications were used to deduce independent linear transformations for precursor and fragment masses that would minimize the mean square deviation of measured masses from theoretical. Re-calibrated mass list files were searched against the same human protein database by a combination of Mascot and Phenyx (GeneBio, SA, version 2.5.14) search engines using narrower mass tolerances (±4 ppm and ±0.3 Da). One missed tryptic cleavage site was allowed. Carbamidomethyl cysteine was set as a fixed modification and oxidized methionine was set as a variable modification. To validate the proteins, Mascot and Phenyx output files were processed by internally-developed parsers. Proteins with ≥2 unique peptides above a score T1, or with a single peptide above a score T2 were selected as unambiguous identifications. Additional peptides for these validated proteins with score >T3 were also accepted. For Mascot searches, the following thresholds were used: T1=14, T2=40 and T3=10; Phenyx thresholds were set to 4.2, 4.75 and 3.5, respectively (P-value<10-3). The validated proteins retrieved by the two algorithms were merged, any spectral conflicts discarded and grouped according to shared peptides. A false discovery rate (FDR) of <1% for protein identifications and <0.1% for peptides (including the ones exported with lower scores) was determined by applying the same procedure against a database of reversed protein sequences.

Non-specific binders were filtered from the drug pulldowns using the SAINT software (version 2.3.4) Using protein spectral counts as a measure of protein abundance and comparing the data of a real pull-down versus the negative control experiments, SAINT calculates the probability of a prey protein to be a real bait interactor. We also compared SAINT probabilities with the fold-reduction of spectral count upon free compound competition representing a magnitude of effect. Fold-reduction was computed as the ratio of median spectral counts observed in pull-downs with/without competition. In each condition, 4 spectral counts were available for the median (2 biological replicates and 2 technical for each).

Cellular Thermoshift Assays

Cellular thermoshift assays were performed as described in the literature (Martinez Molina et al Science 2013). Briefly, alpha cell lysates were warmed to the indicated temperatures in the range of 40-64 degrees Celsius and precipitated proteins removed by centrifugation. Supernatants were used in Western blot analysis probed for the levels of Btbd9 (Abcam), Cul3, and gephyrin (Synaptic system) with specific antibodies.

Co-Immunoprecipitation

Alpha cell lysates pre-treated with either artmether or control DMSO were used and immunoprecipitation was performed with a specific antibody directed against Btbd9 (Abnova). Antibody-complexes were immobilized on Protein A Dynabeads, washed and eluted with SDS-containing loading buffer. Bound proteins amounts were estimated by comparison to 5% input samples. Western blotting with a specific antibody directed against CUL3 was used to determine the interaction between BTBD9 and CUL3.

Statistical Methods

All the p-values were calculated by student t test, unless specified as other methods. The Gene ontology terms enrichment was performed using Gorilla.

Results

To discriminate cell-autonomous effects of Pax4 and Arx overexpression from phenotypes that require paracrine and endocrine signaling in an islet microenvironment, we engineered mouse beta cell line Min6 to allow inducible overexpression of PAX4, ARX or control GFP (FIG. 1a and FIG. 1b). In these cell lines we measured the gene expression changes induced by transcription factor overexpression for one (FIG. 1c), three, and six days. More than 800 genes were oppositely regulated by PAX4 and ARX at the early 24 h timepoint indicative of direct regulation by the two factors (FIG. 1d). Interestingly, the endocrine progenitor factor Ngn3 was among the top genes differentially regulated by the two transcription factors. While PAX4 overexpression repressed Ngn3, ARX overexpression transiently activated this factor (FIGS. 1e and 1f). One possible explanation of Ngn3 activation is that beta cells acquire increased plasticity following ARX overexpression. Furthermore, ARX induction repressed Pax4 after 24 h and activated transcription of several alpha cell genes including glucagon at the later time point of 6 days (FIG. 1g). These changes are indicative of our system faithfully modeling the beta to alpha fate switch upon ARX overexpression which was previously only observed in animal models. Thereby, we have generated a cellular system allowing high-throughput and high content screening for functional repressors of ARX. To identify such compounds, we induced ARX expression at the same time when we added compounds and then measured insulin levels after 72 hours. In control DMSO-treated samples we observed a 50% drop in insulin levels compared to uninduced cells (FIG. 2a). We then screened a library of 280 clinically approved small molecules selected for their structural and target diversity. Hit compounds were selected for their ability to maintain high insulin levels even in the presence of ARX while not affecting cell viability (FIG. 2b). Interestingly, two artemisinins, artemether and dihydroartemisinin, are among the top hits, fully inhibiting the ARX overexpression phenotype. These are the only hit compounds that also induce insulin and Pax4 expression in pancreatic alpha cells, as predicted for functional inhibitors of ARX (FIG. 2c, d). Based on these findings, we investigated the effects of additional artemisinin analogs in alpha and beta cells. While artesunate shows similar effects (FIG. 3a), analogs lacking the endoperoxide moiety like Deoxyartemether showed no effects on insulin expression in alpha cells (FIG. 3b). A dose-response assay indicated half maximum effective concentrations below 1 uM in Min6 cells overexpressing ARX (FIG. 3c) and below 10 uM in alpha cells (FIG. 3d).

Despite being widely used in the treatment of malaria, the molecular mechanism of action of artemisinins is not clear. Different molecular targets have been proposed including the oxidation of iron in human erythrocytes and the inhibition of the *plasmodium* endoplasmatic reticulin Ca2+ ATPase SERCA (O'Neill et al., 2010). In addition, potent effects of these compounds on mammalian cells are observed, and artemisinins have been described as anti-inflammatory and anti-cancer agents. The effect of isolated artemisinins in the pancreas has not yet been evaluated, but limited evidence exist for positive effects of *Artemisia* extracts in human patients and in an animal models of type 1 diabetes (Ahmad et al., 2014). To identify the molecular mechanism of action of artemisinins in pancreatic alpha cells, we used a chemical proteomics approach. We coupled artesunate, an artemisinin active in alpha cells and Arx-overexpressing beta cells, to solid support and performed pull-down experiments in the presence and absence of competing free artemether (FIG. 4a). Mass spectrometry identified gephyrin as the top specific interactor, and showed strong enrichment of E3 ubiquiting ligases including CUL3 and its putative substrate adaptor Btbd9 (FIG. 5b). We then used the cellular thermoshift assay (Martinez Molina et al. Science 2013) to confirm these factors as interactors of artemisinins. Typically, interaction with a small molecule stabilizes proteins to thermal unfolding, and we observe such stabilization for BTBD9 following artemether treatment (FIG. 4c). In contrast, gephyring is destabilized (FIG. 4d). Gephyrin exerts different functions including enzymatic activity in the synthesis of the molybdenum cofactor MoCo, regulation of mTOR signaling via interaction with RAFT1, and structural roles in the transport of glycine and GABA receptors to the membrane. In an alpha cell line we observe a dose-dependent increase of gephyrin protein levels following artemisinin treatment by Western blot and immunofluorescence (FIG. 5a and FIG. 5e). This observation is suggestive an artemisinin-mediated increase of gephyrin stability. In accordance, we observe increased MoCo synthesis capacity in compound treated lysates (FIG. 5f). In line with the increased gephyrin levels and clustering, we also observed higher intracellular chlorid ion concentrations (FIG. 5g) and membrane occupancy of GABA receptor (FIG. 5b). To address if alterations in the Cul3-Btbd9 ubiquitination system might be responsible for increased gephyrin stability, we performed co-immunoprecipitation experiments. We observed a strong interaction of BTBD9 with CUL3 that was fully blocked by the addition of artemether (FIG. 5c).

RNA-Sequencing experiments of alpha cells further underlined the effects of artemether on GABA receptor signaling. Gene set enrichment analysis identifies the synaptic transmission process among the significantly altered pathways, and we observed a significant upregulation of genes Nrxn3, Sv2b and Shc3 in the pathway (FIG. 5d). Interestingly, GABA has been proposed as a factor that can reverse diabetes by induction of beta cell proliferation (Soltani et al., 2011). To prove that GABA receptor signaling plays a role in the mechanism of action of artemisinins in pancreatic alpha cells, we combined artemether with bicuculline (FIG. 5h) or gabazine (FIG. 5i), two GABA receptor antagonists. The presence of GABA receptor antagonists inhibited the effects of artemether in TC1 cells. Importantly, the treatment of thiagabine, a GABAR agonist, also increased the insulin expression in alpha cells (FIG. 5j). To characterize the relevance of our finding for human biology, we examined the effects of artemether in human primary pancreatic islets. In line with the findings in mouse cell lines, we observed increased levels of gephyrin protein) and increased membrane staining for GABA receptor (FIG. 6b). 3-day treatment with artemether increased the secretion of insulin (FIG. 6b) and the number of double-positive cells expressing both insulin and glucagon (FIG. 6a,d). On the gene expression level, artemether-treated islet cultures overall dramatically reduced the expression of alpha cell factors ARX and PPY, while there is slightly increased expression of beta cell factors including PAX6 and PAX4.

Artemisinin combination therapy is the treatment of choice for malaria and more than 300 million treatments are dispensed annually. Despite this large patient cohort, no clinical data on the effects of artemisinins on human pancreatic endocrine function have been published and for several reasons such might have gone unnoticed so far. The acute life-threatening condition of *plasmodium* infected patients together with the known propensity of *plasmodium* infection to cause hypoglycemia make blood glucose levels highly variable in the short term. Furthermore, in healthy individuals even a dramatic increase in beta cell number is not expected to cause a phenotype, as they only secrete insulin in a glucose-regulated manner. Unfortunately, currently no imaging methods are available to directly assess human beta cell mass. The ideal subject to study artemisinin effects on pancreatic function would be a type 1 diabetes patient with a complete absence of detectable insulin C-peptide, a condition that affects approximate 60% of T1D patients or one in 1500 children. We are currently trying to obtain blood samples from such patients who additionally are infected for malaria and receive treatment with artemisinin combination therapies. If artemsinins also induce trans-differentiation, we expect to be able to detect C-peptide in post-treatment blood samples but not in samples taken at diagnosis.

The short treatment cycle, negative effects of the *plasmodium* or other drugs in combination treatment or achievable artemisinin levels in the pancreas might still limit the clinical usefulness in this setting. However, even in that case our findings open up completely new avenues for drug discovery towards a treatment for type 1 diabetes by trans-differentiating alpha to beta cells. These could include structurally different gephyrin stabilizers but also compounds that target other players in the GABA receptor signaling pathway.

REFERENCES

Ahmad, W., Khan, I., Khan, M. A., Ahmad, M., Subhan, F., and Karim, N. (2014). Evaluation of antidiabetic and antihyperlipidemic activity of *Artemisia indica* linn (aeriel parts) in Streptozotocin induced diabetic rats. J Ethnopharmacol. 151: 618-623.

Al-Hasani, K., Pfeifer, A., Courtney, M., Ben-Othman, N., Gjernes, E., Vieira, A., Druelle, N., Avolio, F., Ravassard, P., Leuckx, G., et al. (2013). Adult Duct-Lining Cells Can Reprogram into beta-like Cells Able to Counter Repeated Cycles of Toxin-Induced Diabetes. Dev Cell 26, 86-100.

Arancibia-Cárcamo, I. L., Yuen, E. Y., Muir, J., Lumb, M. J., Michels, G., Saliba, R. S., Smart, T. G., Yan, Z., Kittler, J. T., Moss, S. J. (2009). Ubiquitin-dependent lysosomal targeting of GABA(A) receptors regulates neuronal inhibition. Proc Natl Acad Sci USA. 106:17552-17557. Collombat, P., Xu, X., Ravassard, P., Sosa-Pineda, B., Dussaud, S., Billestrup, N., Madsen, O. D., Serup, P., Heimberg, H., and Mansouri, A. (2009). The ectopic expression of Pax4 in the mouse pancreas converts progenitor cells into alpha and subsequently beta cells. Cell 138, 449-462.

Courtney, M., Gjernes, E., Druelle, N., Ravaud, C., Vieira, A., Ben-Othman, N., Pfeifer, A., Avolio, F., Leuckx, G., Lacas-Gervais, S., et al. (2013). The Inactivation of Arx in Pancreatic alpha-Cells Triggers Their Neogenesis and Conversion into Functional beta-Like Cells. PLoS Genet 9, e1003934.

Forstera, B., Belaidi, A. A., Juttner, R., Bernert, C., Tsokos, M., Lehmann, T. N., Horn, P., Dehnicke, C., Schwarz, G., and Meier, J. C. (2010). Irregular RNA splicing curtails postsynaptic gephyrin in the cornu ammonis of patients with epilepsy. Brain 133,3778-3794.

Genau, H. M., Huber, J., Baschieri, F., Akutsu, M., Dotsch, V., Farhan, H., Rogov, V., Behrends, C. (2015). CUL3-KBTBD6/KBTBD7 Ubiquitin Ligase Cooperates with GABARAP Proteins to Spatially Restrict TIAM1-RAC1 Signaling. Mol Cell 57:995-1010.

Huber, K et al. (2014) Stereospecific targeting of MTH1 by (5)-crizotinib as anticancer strategy. Nature, 508, 222-227.

Martinez Molina, D., Jafari, R., Ignatushchenko, M., Seki, T., Larsson, E. A., Dan, C., Sreekumar, L., Cao, Y, Nordlund, P. (2013) Monitoring drug target engagement in cells and tissues using the cellular thermal shift assay. Science. 341, 84-7.

O'Neill, P. M., Barton, V. E., and Ward, S. A. (2010). The molecular mechanism of action of artemisininthe debate continues. Molecules 15, 1705-1721.

Pagliuca, F. W., and Melton, D. A. (2013). How to make a functional beta-cell. Development 140, 2472-2483.

Reiss, J., and Johnson, J. L. (2003). Mutations in the molybdenum cofactor biosynthetic genes MOCS1, MOCS2, and GEPH. Hum Mutat 21, 569-576.

Soltani, N., Qiu, H., Aleksic, M., Glinka, Y., Zhao, F., Liu, R., Li, Y., Zhang, N., Chakrabarti, R., Ng, T., et al. (2011). GABA exerts protective and regenerative effects on islet beta cells and reverses diabetes. Proc Natl Acad Sci USA 108, 11692-11697.

Stogios, P. J., Downs, G. S., Jauhal, J. J., Nandra, S. K., Privé, G. G. (2005). Sequence and structural analysis of BTB domain proteins. Genome Biol. 6:R82.

Tyagarajan, S. K., and Fritschy, J. M. (2010). GABA(A) receptors, gephyrin and homeostatic synaptic plasticity. J Physiol. 588, 101-106.

Walpita, D., Hasaka, T., Spoonamore, J., Vetere, A., Takane, K. K., Fomina-Yadlin, D., Fiaschi-Taesch, N., Shamji, A., Clemons, P. A., Stewart, A. F., et al. (2012). A human islet cell culture system for high-throughput screening. J Biomol Screen 17, 509-518.

Zhou, Q., Brown, J., Kanarek, A., Rajagopal, J., and Melton, D. A. (2008). In vivo reprogramming of adult pancreatic exocrine cells to beta-cells. Nature 455, 627-632.

The invention claimed is:

1. A method of treating a patient suffering from diabetes or a diabetes associated disorder, comprising administering an artemisinin compound of general formula I

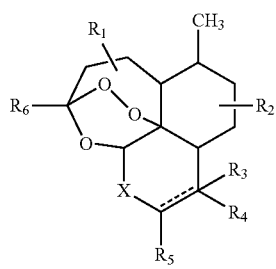

(I)

or a pharmaceutically acceptable salt thereof, wherein:

$\text{-----}$ is a single or double bound;

$R_1$, $R_2$, $R_3$, $R_4$, and $R_6$ represent independently from one another H, halogen, $-CF_3$, $=CH_2$, $-OR^a$, $-NR^aR^b$, $-(CH_2)_nCOOR^a$, $-(CH_2)_nC(=O)R^a$, $-(CH_2)_n$ CONR$^a$R$^a$, $C_{1-6}$alkyl, $C_{2-6}$alkenyl, $C_{2-6}$alkynyl, $C_{3-7}$cycloalkyl, $C_{3-7}$heterocycloalkyl, aryl or heteroaryl; and $R_5$ represents H, halogen, $=O$, $-OR^a$, $-NR^aR^b$, $-(CH_2)_nCF_3$, $-(CH_2)_nCHF_2$, $-(CH_2)_nC(=O)R^a$, $-O(CH_2)_nCOOR^a$, $-OC(=O)(CH_2)_nCOOR^a$, $-OC(=O)R^a$, $C_{1-6}$alkyl, $C_{2-6}$alkenyl, $C_{2-6}$alkynyl, $C_{3-7}$cycloalkyl, $C_{3-7}$heterocycloalkyl, aryl or heteroaryl; and X represents O or $-NR^a$;

$R^a$ represents H or optionally substituted $C_{1-6}$alkyl, $C_{2-6}$alkenyl, or $C_{2-6}$alkynyl; and $R^b$ represents H or an optionally substituted $C_{1-6}$alkyl, $C_{2-6}$alkenyl, $C_{2-6}$alkynyl, cycloalkyl, aryl, heteroaryl or aralkyl; or $R^a$ and $R^b$ together with the interjacent nitrogen atom represent a heterocyclic group, wherein the heterocyclic atom is N, O or S, and wherein the heterocyclic atom is optionally substituted (artemisone); and n is 0, 1, 2 or 3.

2. The method of claim 1, wherein the patient is suffering from diabetes type I, diabetes type 2, a C-peptide negative or C-peptide positive diabetes, or diabetes-associated disorders.

3. The method of claim 1, wherein the compound is administered to the patient to treat hypoinsulinemia, by systemic or local administration.

4. The method of claims 1, wherein the compound is selected from the group consisting of artelinic acid, artemether, artemotil, artenimol, artemisone and artesunate, or a pharmaceutically acceptable salt thereof.

5. The method of claims 1, wherein the compound is coupled to a ligand or carrier moiety.

6. The method of claims 1, wherein the compound is administered in a pharmaceutical preparation for oral, parenteral, systemic, mucosal, topic, rectal, sublingual, buccal or implant use which preparation comprises a pharmaceutically acceptable carrier.

7. The method of claims 1, wherein the compound is administered at a dose at least once per day, in a single dose or multiple doses, or wherein the dose is provided in a slow-release formulation or device.

8. The method of claims 1, wherein the treatment is combined with another anti-diabetic therapy.

9. The method of claims 1, wherein the compound is administered in combination with another gephyrin agonist or BTBD9 inhibitor.

10. The method of claim 1, wherein the compound is administered to the patient in a therapeutically effective amount to increase the insulin expression or level.

11. The method of claim 1, wherein the compound is administered to the patient in a therapeutically effective amount to increase the insulin level.

12. The method of claim 6, wherein the pharmaceutical preparation is a tablet, dermal or transdermal formulation, ointment, gel, cream, lotion, patch, solution, injectable, ophtalmic solution, disperse system, emulsion, microencapsulated drug system, osmotic pump, subdermal implant, granule, microsphere, modified- release system, targeted release system, granules, or pill.

13. The method of claim 7, wherein the dose is 0.1-500 mg/day.

14. The method of claim 8, wherein the other anti-diabetic therapy comprises treatment with insulin, sulfonylureas, incretins, other secretagogues, glitazones, metformin, GLP-1 agonists or DPP4 inhibitors, glucosidease inhibitors, amylin analogs, SGLT2 inhibitors, gastric bypass surgery or pancreatic island transplantation.

15. The method of claim 7, wherein the compound is administered at a dose of 0.01-2000 mg/day.

16. The method of claim 15, wherein the compound is administered at a dose of 0.1-500 mg/day.

17. A method of treating a diabetes patient to increase the insulin level, comprising administering a pharmaceutical combination preparation comprising:

a) an artemisinin compound of general formula I (I)

or a pharmaceutically acceptable salt thereof,
wherein:
----- is a single or double bound;
$R_1$, $R_2$, $R_3$, $R_4$, and $R_6$ represent independently from one another H, halogen, —$CF_3$, =$CH_2$, —$OR^a$, —$NR^aR^b$, —$(CH_2)_nCOOR^a$, —$(CH_2)_nC(=O)R^a$, —$(CH_2)_n$CONR$^a$R$^a$, $C_{1-6}$alkyl, $C_{2-6}$alkenyl, $C_{2-6}$alkynyl, $C_{3-7}$cycloalkyl, $C_{3-7}$heterocycloalkyl, aryl or heteroaryl; and $R_5$ represents H, halogen, =O, —$OR^a$, —$NR^aR^b$, —$(CH_2)_nCF_3$, —$(CH_2)_nCHF_2$, —$(CH_2)_nC(=O)R^a$, —$O(CH_2)_nCOOR^a$, —OC(=O)$(CH_2)_nCOOR^a$, —OC(=O)$R^a$, $C_{1-6}$alkyl, $C_{2-6}$alkenyl, $C_{2-6}$alkynyl, $C_{3-7}$cycloalkyl, $C_{3-7}$heterocycloalkyl, aryl or heteroaryl; and X represents O or —$NR^a$;

$R^a$ represents H or optionally substituted $C_{1-6}$alkyl, $C_{2-6}$alkenyl, or $C_{2-6}$alkynyl; and $R^b$ represents H or an optionally substituted $C_{1-6}$alkyl, $C_{2-6}$alkenyl, $C_{2-6}$alkynyl, cycloalkyl, aryl, heteroaryl or aralkyl; or $R^a$ and $R^b$ together with the interjacent nitrogen atom represent a heterocyclic group, wherein the heterocyclic atom is N, O or S, and wherein the heterocyclic atom is optionally substituted (artemisone); and n is 0, 1, 2 or 3; and b) another BTBD9 inhibitor or gephyrin agonist which is an agent that:

i) inhibits the binding of BTBD9 to CUL3; and/or
 ii) increases the level or clustering of gephyrin; and/or
 iii) increases, enhances, stimulates, or promotes binding of gephyrin to the receptor of the gamma-aminobutyric acid (GABAR); and/or
 iv) increases gephyrin-mediated signaling of the GABAR.

18. A method of treating a neurological disorder comprising administering a DTBD9 binding or gephyrin binding active agent.

19. The method of claim 18, wherein the BTBD9 binding or gephyrin binding active agent is a small molecule.

20. The method of claim 18, wherein the BTBD9 binding or gephyrin binding active agent is an artemisinin compound of general formula I (I)

or a pharmaceutically acceptable salt thereof,
wherein:
----- is a single or double bound;
$R_1$, $R_2$, $R_3$, $R_4$, and $R_6$ represent independently from one another H, halogen, —$CF_3$, =$CH_2$, —$OR^a$, —$NR^aR^b$, —$(CH_2)_nCOOR^a$, —$(CH_2)_nC(=O)R^a$, —$(CH_2)_n$CONR$^a$R$^a$, $C_{1-6}$alkyl, $C_{2-6}$alkenyl, $C_{2-6}$alkynyl, $C_{3-7}$cycloalkyl, $C_{3-7}$heterocycloalkyl, aryl or heteroaryl; and $R_5$ represents H, halogen, =O, —$OR^a$, —$NR^aR^b$, —$(CH_2)_nCF_3$, —$(CH_2)_nCHF_2$, —$(CH_2)_nC(=O)R^a$, —$O(CH_2)_nCOOR^a$, —OC(=O)$(CH_2)_nCOOR^a$, —OC(=O)$R^a$, $C_{1-6}$alkyl, $C_{2-6}$alkenyl, $C_{2-6}$alkynyl, $C_{3-7}$cycloalkyl, $C_{3-7}$heterocycloalkyl, aryl or heteroaryl; and X represents O or —$NR^a$;

$R^a$ represents H or optionally substituted $C_{1-6}$alkyl, $C_{2-6}$alkenyl, or $C_{2-6}$alkynyl; and $R^b$ represents H or an optionally substituted $C_{1-6}$alkyl, $C_{2-6}$alkenyl, $C_{2-6}$alkynyl, cycloalkyl, aryl, heteroaryl or aralkyl; or $R^a$ and $R^b$ together with the interjacent nitrogen atom represent a heterocyclic group, wherein the heterocyclic atom is N, O or S, and wherein the heterocyclic atom is optionally substituted (artemisone); and n is 0, 1, 2 or 3.

21. The method of claim 18, wherein the neurological disorder is selected from the group consisting of temporal lobe epilepsy, sleep disorders, panic attacks, seizures, muscle spasms, Moco deficiency, and alcoholism.

* * * * *

UNITED STATES PATENT AND TRADEMARK OFFICE
CERTIFICATE OF CORRECTION

PATENT NO. : 9,999,621 B2
APPLICATION NO. : 15/303170
DATED : June 19, 2018
INVENTOR(S) : Jin Li et al.

Page 1 of 1

It is certified that error appears in the above-identified patent and that said Letters Patent is hereby corrected as shown below:

In the Claims

In Claim 4, Column 43, Line 4, delete "claims" and insert --claim-- therefor.
In Claim 5, Column 43, Line 8, delete "claims" and insert --claim-- therefor.
In Claim 6, Column 43, Line 10, delete "claims" and insert --claim-- therefor.
In Claim 7, Column 43, Line 15, delete "claims" and insert --claim-- therefor.
In Claim 8, Column 43, Line 19, delete "claims" and insert --claim-- therefor.
In Claim 9, Column 43, Line 21, delete "claims" and insert --claim-- therefor.
In Claim 17, Column 43, Line 65, delete "bound" and insert --bond-- therefor.
In Claim 20, Column 44, Line 55, delete "bound" and insert --bond-- therefor.

Signed and Sealed this
Fourth Day of September, 2018

Andrei Iancu
*Director of the United States Patent and Trademark Office*